United States Patent [19]

Burdeska et al.

[11] 4,366,189
[45] Dec. 28, 1982

[54] 4-HETEROCYCLYL-4'-VINYLSTILBENES

[75] Inventors: Kurt Burdeska, Basel; Guglielmo Kabas, Aesch; Kurt Weber, Basel, all of Switzerland

[73] Assignee: Ciba-Geigy Corporation, Ardsley, N.Y.

[21] Appl. No.: 214,946

[22] Filed: Dec. 10, 1980

[30] Foreign Application Priority Data

Dec. 21, 1979 [CH] Switzerland ............ 11402/79
Sep. 18, 1980 [CH] Switzerland ............. 7008/80

[51] Int. Cl.³ ..................................... B05B 5/00
[52] U.S. Cl. ............................. 427/157; 252/301.21; 427/158; 427/381; 427/389.9; 427/391; 427/392; 542/444; 542/455; 542/456; 542/459; 542/464; 544/321
[58] Field of Search ............ 542/459, 464, 444, 455, 542/456, 458; 544/321; 252/301.21, 301.22, 301.16, 301.33, 102

[56] References Cited

U.S. PATENT DOCUMENTS

| | | | |
|---|---|---|---|
| 3,697,513 | 10/1972 | Siegrist ................... | 542/459 |
| 3,984,399 | 10/1976 | Weber et al. ............. | 542/459 |
| 4,014,870 | 3/1977 | Meyer ..................... | 162/162 X |
| 4,032,558 | 6/1977 | Fleck et al. ............. | 542/459 X |
| 4,108,887 | 8/1978 | Fleck et al. ............. | 260/465 H |
| 4,113,837 | 9/1978 | Kendall et al. .......... | 423/226 |
| 4,172,045 | 10/1979 | Meyer et al. ............ | 252/301.22 X |
| 4,196,229 | 4/1980 | Fleck et al. ............. | 427/158 |
| 4,206,072 | 6/1980 | Meyer et al. ............ | 252/301.24 |
| 4,261,853 | 4/1981 | Kontz et al. ............. | 252/182.1 |

FOREIGN PATENT DOCUMENTS 206431 7/1965 U.S.S.R. ................. 542/459

OTHER PUBLICATIONS

The Condensed Chemical Dictionary, Rose and Rose, 6th Ed., p. 275, Reinhold Publishing Corp.

*Primary Examiner*—Thurman K. Page
*Attorney, Agent, or Firm*—Edward McC. Roberts

[57] ABSTRACT

The invention relates to 4-heterocyclyl-4'-vinylstilbenes of the formula

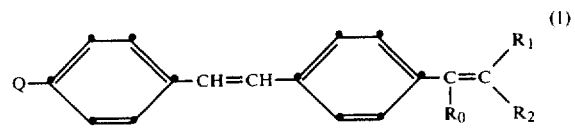

wherein Q is a monocyclic 5- or 6-membered aromatic heterocyclic ring which is unsubstituted or substituted by non-chromophoric groups and which contains no fused benzene rings or 1 or 2 fused benzene rings, or is a bicyclic 9-membered aromatic heterocyclic ring, phenyl which is unsubstituted or substituted by non-chromophoric groups, or is cyano, carboxyl, alkoxycarbonyl or alkylsulfonyl or arylsulfonyl, $R_o$ is hydrogen, alkyl which is unsubstituted or substituted by non-chromophoric groups, $R_1$ is hydrogen, alkyl, alkoxycarbonyl, carbamoyl or sulfonamide, each of which is unsubstituted or substituted by non-chromophoric groups, or is alkenyl, carboxyl, alkylsulfonyl, arylsulfonyl or aralkylsulfonyl, cyano, sulfo or phosphonic acid dialkyl ester, and $R_2$ is hydrogen, alkyl or alkenyl, each of which is unsubstituted or substituted by non-chromophoric groups, with the proviso that at most one of $R_1$ and $R_2$ is hydrogen. These compounds are used for whitening organic material of high molecular weight, especially polyester. They can be employed in admixture with other fluorescent whitening agents.

20 Claims, No Drawings

4-HETEROCYCLYL-4′-VINYLSTILBENES

The present invention relates to 4-heterocyclyl-4′-vinylstilbenes, to a process for the production thereof, and to the use thereof for whitening natural and synthetic organic material.

The invention has for its object to provide novel fluorescent whitening agents with improved exhaustion properties. It has been found that heterocyclyl-stilbenes containing a vinyl substituent at one of the terminal phenyl radicals are more productive than hitherto known heterocyclyl-stilbenes.

The novel 4-heterocyclyl-4′-vinylstilbenes have the formula

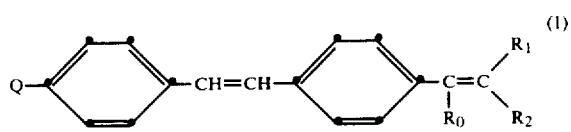

wherein Q is a monocyclic 5- or 6-membered aromatic heterocyclic ring which is unsubstituted or substituted by non-chromophoric groups and which contains no fused benzene rings or 1 or 2 fused benzene rings, or is a bicyclic 9-membered aromatic heterocyclic ring, phenyl which is unsubstituted or substituted by non-chromophoric groups, or is cyano, carboxyl, alkoxycarbonyl, alkylsulfonyl or arylsulfonyl, $R_o$ is hydrogen, alkyl which is unsubstituted or substituted by non-chromophoric groups, $R_1$ is hydrogen, alkyl, alkoxycarbonyl, carbamoyl or sulfonamide, each of which is unsubstituted or substituted by non-chromophoric groups, or is alkenyl, carboxyl, alkylsulfonyl, arylsulfonyl, aralkylsulfonyl, cyano, sulfo or phosphonic acid dialkyl ester, and $R_2$ is hydrogen, alkyl or alkenyl, each of which is unsubstituted or substituted by non-chromophoric groups, with the proviso that at most one of $R_1$ and $R_2$ is hydrogen.

Examples of non-chromophoric substituents are: halogen, unsubstituted or substituted alkyl, unsubstituted or substituted alkenyl, aryl or aralkyl, unsubstituted or substituted alkoxy, alkoxycarbonyl, unsubstituted or substituted aminocarbonyl, cyano, alkylsulfonyl, alkoxysulfonyl, unsubstituted or substituted aminosulfonyl, acyl, acylamino, hydroxyl, aryloxy, aralkyloxy, alkenyloxy, aryloxycarbonyl, aralkyloxycarbonyl, carboxyl, acyloxy or trifluoromethyl.

Alkyl is preferably $C_1$-$C_4$alkyl which can be monosubstituted by hydroxyl, $C_1$-$C_4$alkoxy, cyano, carboxyl, $C_1$-$C_4$alkoxycarbonyl, aminocarbonyl, or chlorine.

Alkenyl is preferably $C_2$-$C_5$alkenyl which can be monosubstituted by hydroxyl, $C_1$-$C_4$alkoxy, cyano, carboxyl, $C_1$-$C_4$alkoxycarbonyl or chlorine.

Halogen is preferably fluorine, chlorine or bromine, with chlorine being most preferred. Aryl is preferably phenyl which is unsubstituted or substituted by $C_1$-$C_4$alkyl, chlorine, bromine or $C_1$-$C_4$alkoxy.

Aralkyl is preferably phenyl($C_1$-$C_4$)alkyl which can be additionally substituted in the phenyl nucleus by chlorine, methyl or methoxy.

Alkoxy is preferably $C_1$-$C_4$alkoxy or a radical of the formula —(OCH$_2$—CH$_2$)$_m$—OR, wherein R is hydrogen or $C_1$-$C_4$alkyl and m is an integer from 1 to 20.

Cycloalkyloxy is preferably cyclopentyloxy and cyclohexyloxy.

Acyl is preferably $C_1$-$C_4$alkylcarbonyl, $C_1$-$C_4$alkylsulfonyl, benzoyl which is unsubstituted or substituted by methyl, methoxy or chlorine, or benzenesulfonyl which is unsubstituted or substituted by methyl, methoxy or chlorine.

Eligible substituents of the aminocarbonyl and aminosulfonyl radicals are, in particular, $C_1$-$C_4$alkyl, phenyl or phenyl($C_1$-$C_4$)alkyl, each of which is unsubstituted or substituted by methyl, methoxy or chlorine.

Interesting compounds within the scope of the compounds of the formula I are those of the formula

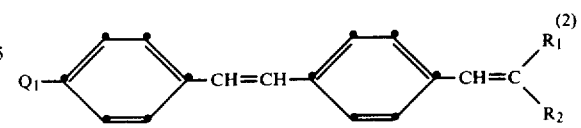

wherein $R_1$ and $R_2$ are as defined above and $Q_1$ is phenyl which is unsubstituted or substituted by non-chromophoric groups, or is cyano, alkoxycarbonyl, alkylsulfonyl or arylsulfonyl, or a radical of the formula

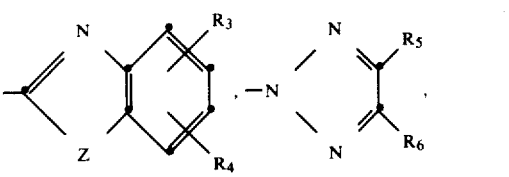

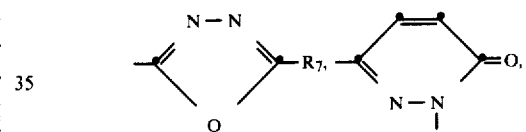

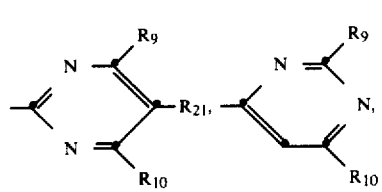

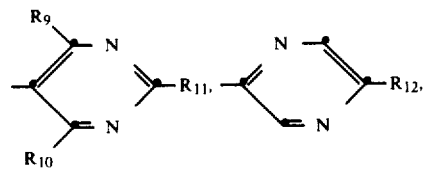

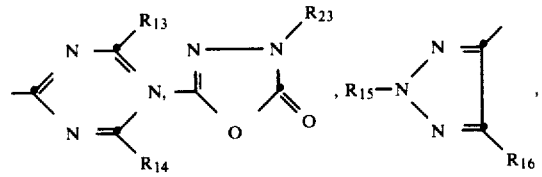

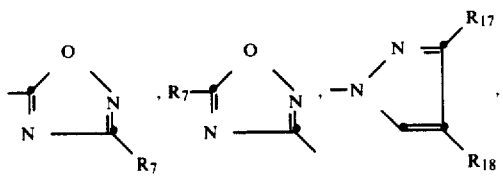

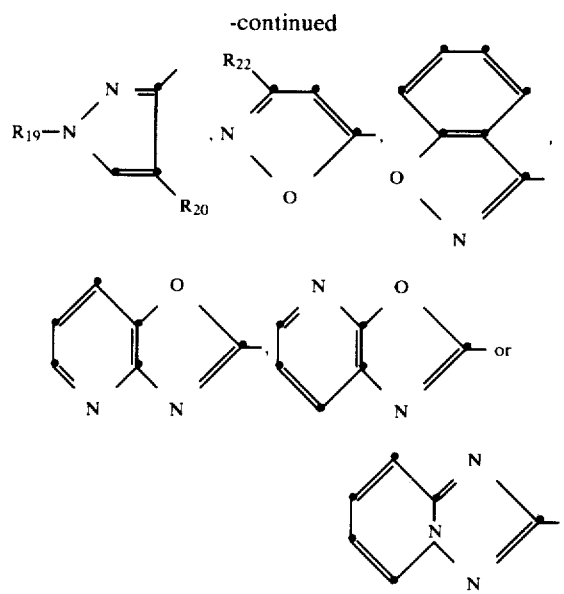

in which formulae

R₃ is hydrogen, chlorine, C₁-C₄alkyl, phenyl(C₁-C₃)alkyl, cyclohexyl, phenyl, C₁-C₄alkoxy, C₁-C₄alkylsulfonyl, C₁-C₄alkoxycarbonyl, cyano or carboxyl, or together with R₄ is a fused 1-cyclopentene, 1-cyclohexene or benzene ring, each of which is unsubstituted or substituted by 1 to 4 methyl groups, R₄ is hydrogen, chlorine or C₁-C₄alkyl or, together with R₃, forms a 1-cyclopentene, 1-cyclohexene or benzene ring, each of which is unsubstituted or substituted by 1 to 4 methyl groups, R₅ is hydrogen, C₁-C₄alkyl, cyano, COOR, wherein R is C₁-C₄alkyl, phenyl or styryl or, together with R₆, forms a fused benzene ring which is unsubstituted or substituted by C₁-C₄alkyl, C₁-C₄alkoxy or chlorine, or a fused naphthalene ring, R₆ is hydrogen, C₁-C₄alkyl, phenyl or, together with R₅, forms a fused benzene ring which is unsubstituted or substituted by C₁-C₄alkyl, C₁-C₄alkoxy or chlorine, or a fused naphthalene ring, R₇ is C₁-C₄alkyl which is unsubstituted or substituted by non-chromophoric groups, phenyl, styryl, biphenylyl or naphthyl, each of which is unsubstituted or substituted by C₁-C₄alkyl, C₁-C₄alkoxy, C₁-C₄alkoxycarbonyl, cyano or chlorine.

R₈ is hydrogen, C₁-C₄alkyl or phenyl which is unsubstituted or substituted by chlorine or methyl, R₉ and R₁₀, each independently of the other, is hydrogen, C₁-C₄alkyl, phenyl which is unsubstituted or substituted by chlorine or methyl, or is C₁-C₄alkoxy, C₃-C₈alkoxyalkoxy, phenoxy which is unsubstituted or substituted by chlorine or methyl, or is chlorine, C₁-C₄alkylthio, phenylthio, C₁-C₄alkylamino, di(C₁-C₄)alkylamino, morpholino, piperidino, piperazino, pyrrolidino or anilino, R₁₁ is hydrogen, C₁-C₄alkyl or phenyl which is unsubstituted or substituted by chlorine or methyl, R₁₂ is C₁-C₄alkoxy, C₃-C₈alkoxyalkoxy, C₁-C₄alkylthio, phenoxy which is unsubstituted or substituted by chlorine or methyl, or is cycloalkoxy, C₁-C₄alkylthio, phenylthio which is unsubstituted or substituted by chlorine or methyl, or is C₁-C₄alkylamino, di(C₁-C₄)alkylamino, morpholino, piperidino, piperazino, pyrrolidino or anilino, R₁₃ and R₁₄ are hydrogen, halogen, C₁-C₄alkoxy, phenyl, aralkoxy, cycloalkoxy, aryloxy, C₁-C₄alkylmercapto, C₁-C₄-alkylamino, di(C₁-C₄)alkylamino, morpholino, piperidino, piperazino, pyrrolidino, arylamino or C₁-C₄alkyl, R₁₅ is phenyl which is unsubstituted or substituted by chlorine or C₁-C₄alkyl, R₁₆ is hydrogen or C₁-C₄alkyl, R₁₇ is phenyl which is unsubstituted or substituted by chlorine or C₁-C₄alkyl, R₁₈ is hydrogen or C₁-C₄alkyl, R₁₉ is phenyl which is unsubstituted or substituted by chlorine or C₁-C₄alkyl, R₂₀ is hydrogen or C₁-C₄alkyl, R₂₁ is hydrogen or C₁-C₄alkyl, R₂₂ is phenyl which is unsubstituted or substituted by C₁-C₄alkoxy, R₂₃ is hydrogen, C₁-C₄alkyl or phenyl which is unsubstituted or substituted by C₁-C₄alkyl, halogen or cyano, and Z is O, S or NX, wherein X is hydrogen, C₁-C₄alkyl, acetyl, benzoyl or phenyl.

Preferred compounds are those of the formula

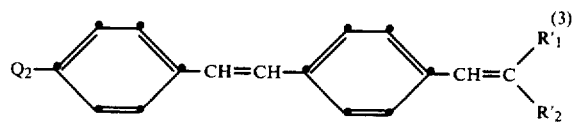

wherein R₁' is hydrogen, C₁-C₆alkyl, C₁-C₆alkyl which is substituted by C₁-C₄alkoxy or C₂-C₅alkoxycarbonyl, or is C₂-C₄alkenyl, cyano, COOR°, wherein R° is C₁-C₄alkyl, C₁-C₄alkoxy-C₂-C₄alkyl, C₁-C₄alkoxy-C₂-C₄alkoxy-C₂-C₄-alkyl, C₁-C₄alkoxy-C₂-C₄alkoxy-C₂-C₄alkoxy-C₂-C₄alkyl, tetrahydro-2-furylmethyl, 1,4-dioxa-2-cyclohexylmethyl, allyl, C₁-C₄alkylamino-C₁-C₄alkyl or di(C₁-C₄)alkylamino-C₁-C₄alkyl, —CON(R')(R''), wherein R' is hydrogen, C₁-C₆alkyl, C₂-C₆alkyl which is substituted by hydroxyl, C₁-C₄alkoxy, C₂-C₆hydroxyalkoxy, —SO₃M or di(C₁-C₄)alkylamino, or is cyclohexyl, benzyl or phenethyl, and R'' is hydrogen, C₁-C₆alkyl, C₂-C₆-alkyl which is substituted by hydroxyl, C₁-C₄alkoxy or C₂-C₆hydroxyalkoxy, —SO₂N(R')(R''), wherein R' and R'' are as defined above, —SO₃M, Rₓ—SO₂—, wherein Rₓ is C₁-C₆alkyl, C₂-C₆alkyl which is substituted by hydroxyl, C₁-C₄alkoxy or C₁-C₄alkoxy-C₂-C₆alkoxy, or is phenyl or benzyl or phosphonic acid dialkyl ester;

R₂' is hydrogen or C₁-C₆alkyl,

M is hydrogen or a non-chromophoric cation common to fluorescent whitening agents, and Q₂ is phenyl, phenyl which is substituted by halogen, C₁-C₄alkyl, C₁-C₄alkoxy, carboxyl, C₂-C₅alkoxycarbonyl or cyano, or is cyano, carboxyl, C₂-C₅alkoxycarbonyl or Rₓ—SO₂—, wherein Rₓ is as defined above, or is a radical of the formula

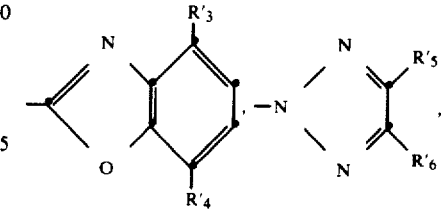

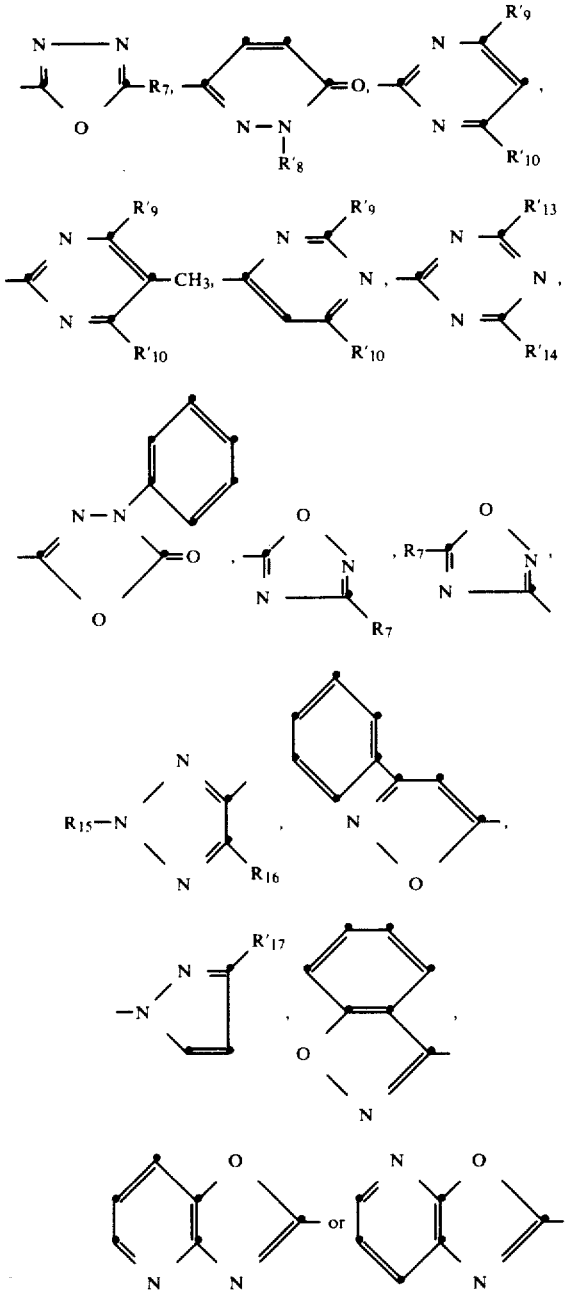

in which formulae

R₃' is hydrogen, methyl, chlorine or C₁-C₄alkoxy,

R₄' is hydrogen, chlorine, C₁-C₄alkyl, phenyl, C₁-C₄alkoxy or phenoxy,

R₅' is hydrogen, C₁-C₄alkyl, phenyl or styryl or, together with R₆, forms a fused unsubstituted benzene ring or a fused benzene ring which is substituted by C₁-C₄alkyl, C₁-C₄alkoxy or chlorine, or a fused naphthalene ring, R₆' is hydrogen, C₁-C₄alkyl, phenyl or, together with R₅', forms a fused unsubstituted benzene ring or a fused benzene ring which is substituted by C₁-C₄alkyl, C₁-C₄alkoxy or chlorine, or a fused naphthalene ring, R₇ is C₁-C₄alkyl which is unsubstituted or substituted by non-chromophoric substituents, phenyl, styryl, biphenyl or naphthyl, each of which is unsubstituted or substituted by C₁-C₄alkyl, C₁-C₄alkoxy, C₁-C₄alkoxycarbonyl, cyano or chlorine.

R₈' is unsubstituted C₁-C₄alkyl or phenyl,

R₉' is hydrogen, unsubstituted C₁-C₄alkyl, phenyl which is unsubstituted or substituted by chlorine or methyl, or is chlorine, C₁-C₄alkoxy, C₃-C₅alkoxyalkoxy, phenoxy which is unsubstituted or substituted by chlorine or methyl, or is C₁-C₄alkylthio or phenylthio, R₁₀' is hydrogen, unsubstituted C₁-C₄alkyl, C₁-C₄alkoxy, phenyl which is unsubstituted or substituted by chlorine or methyl, phenoxy which is unsubstituted or substituted by chlorine or methyl, or is C₁-C₄alkylthio, phenylthio or chlorine, R₁₃' and R₁₄' are hydrogen, C₁-C₄alkylamino, di(C₁-C₄)alkylamino, phenyl, morpholino, piperidino, phenylamino or a radical —(OCH₂—CH₂)$_q$—OY, wherein Y is hydrogen, C₁-C₄alkyl, benzyl or phenyl, and q is an integer from 0 to 7, R₁₅ is phenyl which is unsubstituted or substituted by chlorine or C₁-C₄alkyl, R₁₆ is hydrogen or C₁-C₄alkyl, and R₁₇' is C₁-C₄alkyl.

Further preferred compounds of the formula (1) are those of the formula

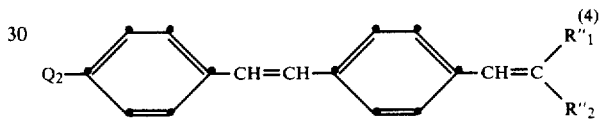
(4)

wherein R₁″ is cyano, COOR, wherein R is C₁-C₄alkyl, C₁-C₄alkoxy-C₂-C₄alkyl, C₁-C₄alkoxy-C₂-C₄alkoxy-C₂-C₄alkyl, C₁-C₄alkoxy-C₂-C₄alkoxy-C₂-C₄alkoxy-C₂-C₄alkyl, 2,3,4,5-tetrahydro-2-furylmethyl, 1,4-dioxa-2-cyclohexylmethyl, CON(R')(R″), wherein R' is hydrogen, C₁-C₆alkyl, C₂-C₆alkyl which is substituted by hydroxyl, C₁-C₄alkoxy, C₂-C₆hydroxyalkoxy, —SO₃M or mono- or di(C₁-C₄)alkylamino, or is cycloalkyl, benzyl or phenethyl, and R″ is hydrogen, C₁-C₆alkyl, C₂-C₆alkyl which is substituted by hydroxyl, C₁-C₄alkoxy or C₂-C₆hydroxyalkoxy, R$_x$—SO₂—, wherein R$_x$ is C₁-C₆alkyl, C₂-C₆alkyl which is substituted by C₁-C₄alkoxy or C₁-C₄alkoxy-C₂-C₆alkoxy, or is phenyl or benzyl or phosphonic acid dialkyl ester; R₂″ is hydrogen or C₁-C₄alkyl, M is hydrogen or a non-chromophoric cation common to fluorescent whitening agents, and Q₂ has the above meaning.

M is preferably hydrogen, an alkali metal cation or an unsubstituted or substituted ammonium cation, e.g. mono-, di- or tri(C₁-C₄alkyl)ammonium or mono-, di- or tri(C₂-C₄alkanol)ammonium, e.g. mono-, di- or triethanolammonium or mono-, di- or triisopropanolammonium, but preferably hydrogen or sodium.

Especially preferred compounds of the invention are (A) those of the formula

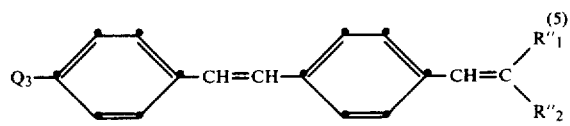
(5)

wherein

R₁″ and R₂″ have the above meanings and Q₃ is phenyl, C₂-C₅-alkoxycarbonyl, cyano or a radical of the formula

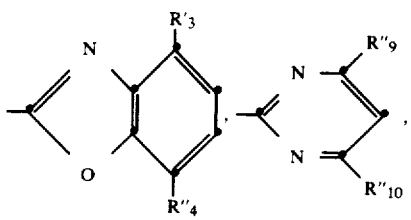

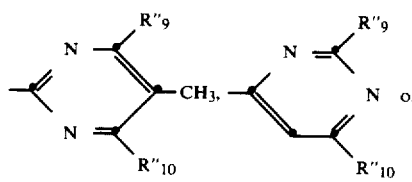

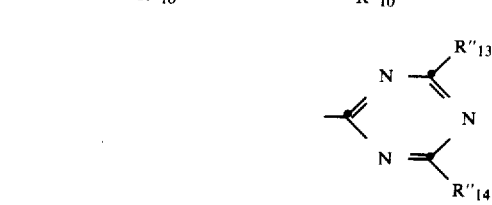

in which formulae R₃′ is hydrogen, methyl, chlorine or C₁-C₄alkoxy, R₄″ is hydrogen, methyl, chlorine or C₁-C₄alkyl, R₉″ is hydrogen, methyl, phenyl, C₁-C₃alkoxy, methoxyethoxy or phenoxy, R₁₀″ is unsubstituted alkyl of 1 or 2 carbon atoms, C₁-C₃alkoxy or phenoxy, and each of R₁₃″ and R₁₄″ is hydrogen or a radical —(OCH₂—CH₂)ᵣ—OY′, wherein Y′ is C₁-C₄alkyl and r is an integer from 0 to 2; and (B) those of the formula

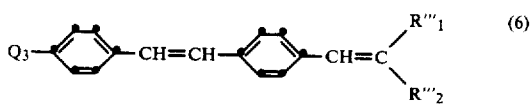

wherein R₁‴ is cyano, COOR, wherein R is C₁-C₄alkyl, C₁-C₄-alkoxy-C₂-C₄alkyl, C₁-C₄alkoxy-C₂-C₄alkoxy-C₂-C₄alkyl, C₁-C₄alkoxy-C₂-C₄alkoxy-C₂-C₄alkoxy-C₂-C₄alkyl, 2,3,4,5-tetrahydro-2-furylmethyl or 1,4-dioxa-2-cyclohexylmethyl or Rₓ—SO₂—, wherein Rₓ is C₁-C₄alkyl, C₂-C₆alkyl which is substituted by C₁-C₄alkoxy or C₁-C₄alkoxy-C₂-C₆alkoxy, or is phenyl or benzyl, and R₂‴ is hydrogen or C₁-C₄alkyl, and Q₃ has the above meaning; and also (C) those of the formula

wherein R₁′ᵛ is cyano or COOR′, wherein R′ is C₁-C₄alkyl or C₁-C₄alkoxy-C₂-C₆alkyl, and Q₃ has the above meaning.

The 4-heterocyclyl-4′-vinylstilbenes of the formula (1) can be obtained by condensing, in the presence of an organic solvent and of a basic condensation agent, a compound of the formula

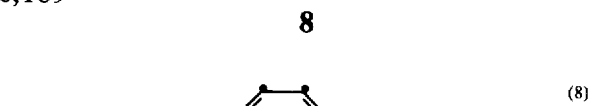

with a compound of the formula

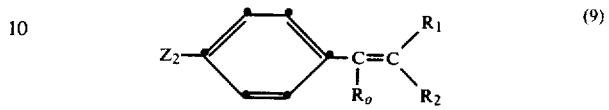

in which formulae Q, R₀, R₁ and R₂ are as defined for formula (1), and one of Z₁ and Z₂ is the OHC group and the other is a grouping of the formula

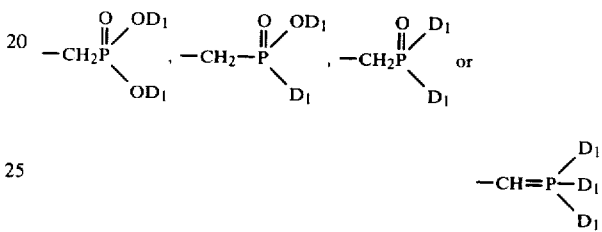

wherein D₁ is an unsubstituted or a substituted alkyl, aryl, cycloalkyl or aralkyl radical.

The solvents employed are advantageously inert solvents, e.g. hydrocarbons such as toluene or xylene, or alcohols such as methanol, ethanol, isopropanol, butanol, glycol, glycol ethers such as 2-methoxyethanol, hexanol, cyclohexanol or cyclooctanol, and also ethers such as diisopropyl ether, dioxane or tetrahydrofurane, and also formamides or N-methylpyrrolidone. Dipolar organic solvents such as dimethyl formamide and dimethyl sulfoxide are particularly suitable.

Suitable condensation agents are strongly basic compounds such as alkali metal hydroxides and alkaline earth metal hydroxides, alkali metal amides and alkaline earth metal amides, alkali metal alcoholates and alkaline earth metal alcoholates, for example potassium hydroxide, sodium hydroxide, potassium tert-butylate, sodium amide or sodium methylate, and also the alkali metal compounds of dimethyl sulfoxide and alkali metal hydrides and, if appropriate, alkali metal dispersions.

The reaction is preferably carried out in the temperature range from 0° to 100° C. The compounds of the invention are also obtained by using the corresponding quaternary phosphonium salts, for example the triphenylphosphonium salts, instead of the phosphono compounds (8) and (9), and condensing these salts with the aldehydes (9) or (8) via the phosphorylene intermediates.

It is, of course, also possible to subject the reaction products obtained from the above processes to further conversion reactions which are known per se, such as halogenating reactions, functional modifications of carboxyl groups, the introduction of chloromethyl groups or the replacement of halogen atoms by cyano groups.

However, compounds of the formula (1) can also be prepared by other processes which are known per se. For example, it is possible to react a Schiff's base of the formula

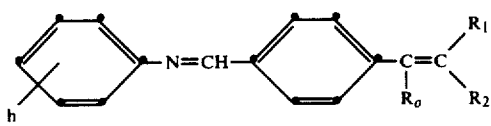

wherein $R_o$, $R_1$ and $R_2$ have the above meanings and h is preferably hydrogen or chlorine, with a methyl compound of the formula

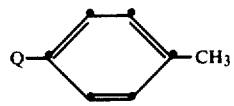

wherein Q is as defined above, in the presence of a strongly basic alkali metal compound in dimethyl formamide as the reaction medium. In this context, strongly basic alkali metal compounds are to be understood as meaning those compounds of the alkali metals which have a strength at least approximately equal to that of lithium hydroxide. The compounds can accordingly be compounds of lithium, sodium, potassium, rubidium or caesium of the alcoholate, hydroxide or strongly basic ion exchanger type. It is advantageous to use potassium compounds having the composition

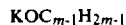

in which m is an integer from 1 to 6, for example potassium hydroxide or potassium tertiary butylate. If alkali metal alcoholates are used, the reaction must be carried out in a virtually anhydrous medium; but when using alkali metal hydroxides, water contents of up to 25% (for example contents of water of crystallisation) are permissible. A water content of up to about 10% is advantageous when using potassium hydroxide. Examples of other alkali metal compounds which can be used are: sodium methylate, sodium hydroxide, lithium hydroxide, rubidium hydroxide, caesium hydroxide and the like. It will be understood that mixtures of such bases can also be used in the reaction.

The compounds of the formula (11), wherein Q is a radical of the formula

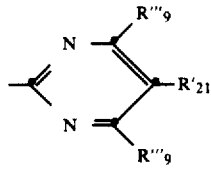

wherein $R_9'''$ is hydrogen, $C_3$-$C_4$-alkyl or $C_1$-$C_4$alkylthio, and $R_{21}'$ is hydrogen or methyl, are novel and likewise constitute an object of the present invention.

The compounds of the formula (11) are advantageously reacted with the Schiff's base of the formula (10) in equivalent amounts, so that there is no substantial excess of either component. It is advantageous to use at least the equivalent amount of the alkali metal compound, i.e. at least 1 mole of a compound containing e.g. a KO group per mole of Schiff's base. If potassium hydroxide is used, it is preferably present in the 4-fold to 8-fold amount. In general, the reaction can be carried out in the temperature range from about 10° to 150° C. If an alcoholate is used as the potassium compound for the reaction, it is generally not necessary to apply heat. The procedure is, for example, to add the Schiff's base of the formula (10) to the mixture of the compound of the formula (11), the solvent and the potassium alcoholate, advantageously with stirring and with the exclusion of air, in the temperature range from 15° to 30° C., whereupon the reaction takes place straightaway, accompanied by a slight rise in temperature. When potassium hydroxide is employed, it is frequently necessary to carry out the reaction at a higher temperature. For example, the reaction mixture is slowly warmed to 30° to 100° C. and then kept at this temperature for some time, for example ½ hour to 2 hours. The final products can be isolated from the reaction mixture by conventional methods which are known per se.

The compounds of the formula (1) can also be obtained by Heck's reaction, by reacting an aromatic halide with an acrylic acid derivative in the presence of a palladium derivative, e.g. palladium acetate, as catalyst [cf. R. F. Heck and J. -P. Nolley, Jr., J. Org. Chem., 37, 2320-2322 (1972)].

The novel compounds defined above exhibit a more or less pronounced fluorescence in the dissolved or finely divided state. They can be used for whitening and/or brightening a wide variety of synthetic, regenerated man-made or natural organic materials or substances which contain such organic materials.

Without any restriction being implied by the following classification, examples of organic materials which can be treated with fluorescent whitening agents are:

I. Man-made organic material of high molecular weight:
(a) polymerisation products based on organic compounds containing at least one polymerisable carbon-carbon double bond, that is to say their homopolymers of copolymers as well as their aftertreatment products, for example, crosslinking, grafting or degradation products, polymer blends, or products obtained by modification of reactive groups, for example polymers based on α,β-unsaturated carboxylic acids or derivatives of such carboxylic acids, especially on acrylic compounds, for example acrylates, acrylic acid, acrylonitrile, acrylamides and their methacrylic analogues, of olefin hydrocarbons (for example ethylene, propylene, styrenes or dienes and also ABS polymers), and polymers based on vinyl and vinylidene compounds (for example vinyl chloride, vinyl alcohol and vinylidene chloride);
(b) polymerisation products which can be obtained by ring opening, for example, polyamides of the polycaprolactam type, and also polymers which are obtained both by polyaddition and by polycondensation, for example polyethers or polyacetals;
(c) polycondensation products or precondensates based on bifunctional or polyfunctional compounds with condensable groups, their homocondensation and co-condensation products, and aftertreatment products, for example polyesters, especially saturated polyesters (for example ethylene glycol, terephthalic acid polyester) or unsaturated polyesters (for example maleic acid-dialcohol polycondensates as well as their crosslinking products with copolymerisable vinyl monomers), unbranched and branched polyesters (also including those based on polyhydric alcohols, for example alkyd resins), polyamides (for example hexamethylenediamine adipate), maleic resins, melamine resins, their precondensates and and analogues, polycarbonates and silicones;

(d) polyadducts, such as polyurethanes (crosslinked and uncrosslinked) and epoxy resins.

II. Regenerated man-made organic material, for example, cellulose esters of varying degrees of esterification (so-called 2½-acetate or triacetate) or cellulose ethers, regenerated cellulose (viscose or cuprammonium cellulose), or their aftertreatment products, and casein plastics.

III. Natural organic material of animal or vegetable origin, for example based on cellulose or proteins, such as cotton, wool, linen, silk, natural film-forming resins, starch and casein.

The organic material to be whitened and/or brightened can be in the most diverse states of processing (raw materials, semi-finished goods or finished goods). On the other hand, it can be in the form of structures of the most diverse shapes, for example predominantly three-dimensional structures such as sheets, profiles, injection mouldings, various machined articles, chips, granules or foams, and also predominantly two-dimensional structures, such as films, sheets, lacquers, coatings and impregnations; or predominantly one dimensional bodies such as filaments, fibres, flocks and wires. The above materials can, on the other hand, also be in an unshaped state, in the most diverse homogeneous or inhomogeneous forms of division, as for example in the form of powders, solutions, emulsions, dispersions, latices, pastes or waxes.

Fibrous material can be, for example, in the form of endless filaments (stretched or unstretched), staple fibres, flocks, hanks, textile filament yarns, threads, nonwovens, felts, waddings, flocked structures or woven textile or bonded textile fabrics, knitted fabrics, and papers, cardboards or paper pulps.

The compounds to be used in the practice of this invention are of importance, inter alia, for the treatment of organic textile fabric, especially woven textile fabrics. If it is intended to whiten fibres which can be in the form of staple fibres or endless filaments or in the form of hanks, woven fabrics, knitted fabrics, fleeces, flocked substrates or bonded fabrics, this is advantageously effected in an aqueous medium in which the compounds of the invention are finely dispersed (suspensions, so-called microdispersions, or, optionally, solutions). If desired, dispersing agents, stabilisers, wetting agents and further assistants can be added during the treatment.

Depending on the type of fluorescent whitening agent used, it can be advantageous to carry out the treatment in a neutral or alkaline or acid bath. The treatment is usually carried out in the temperature range from 20° to 140° C., for example at the boiling point of the bath or near it (about 90° C.).

Solutions or emulsions in organic solvents can also be used for the finishing according to the invention of textile substrates, as is practised in the dyeing industry in so-called solvent dyeing (pad-thermofixation application, or exhaust dyeing methods in dyeing machines).

The fluorescent whitening agents of the present invention can further be added to, or incorporated in, the materials before or during their shaping. They can thus be added to the moulding or injection moulding compound in the manufacture of films, sheets (e.g. rolling into polyvinyl chloride at elevated temperature) or moulded articles.

If man-made or regenerated man-made organic materials are formed by spinning processes or from spinning solutions/melts, the fluorescent whitening agents can be applied by the following methods:
  addition to the starting materials (for example monomers) or intermediates (for example precondensates or prepolymers), that is to say before or during the polymerisation, polycondensation or polyaddition,
  sprinkling in powder form on polymer chips or granules for spinning solutions/melts;
  bath dyeing of polymer chips or granules for spinning solutions/melts;
  metered addition to spinning melts or spinning solutions; and
  application to the spun tow before stretching.

The fluorescent whitening agents of the present invention can also be employed e.g. in the following formulations:
(a) in mixtures with dyes (shading) or pigments (coloured pigments or especially, for example, white pigments), or as an additive to dyebaths, printing pastes, discharge pastes or reserve pastes, or for the aftertreatment of dyeings, prints or discharge prints;
(b) in mixtures with carriers, wetting agents, plasticisers, swelling agents, antioxidants, ultraviolet absorbers, heat stabilisers and chemical bleaching agents (chlorite bleach or bleaching bath additives);
(c) in admixture with crosslinking agents or finishing agents (for example starch or synthetic finishes), and in combination with a wide variety of textile finishing processes, especially synthetic resin finishes (for example creaseproof finishes such as wash-and-wear, permanent-press or non-iron), as well as flameproof finishes, soft finishes, anti-soiling finishes or antistatic finishes, or antimicrobial finishes;
(d) incorporation of the fluorescent whitening agent in polymer carriers (polymerisation, polycondensation or polyaddition products, in dissolved or dispersed form, for use e.g. in coating agents, impregnating agents or binders (solutions, dispersions and emulsions) for textiles, nonwovens, papers and leather;
(e) as additives to master batches;
(f) as additives to a wide variety of industrial products in order to render these more marketable (for example improving the appearance of soaps, detergents, pigments);
(g) in spinning bath preparations, that is to say as additives to spinning baths which are used for improving the slip for the further processing of synthetic fibres, or from a special bath before the stretching of the fibre;
(h) as scintillators for various purposes of a photographic nature, for example for electrophotographic reproduction or supersensitising;
(i) depending on the substitution, as laser dyes.

The compounds of the invention can also be employed in combination with other fluorescent whitening agents. Examples of suitable compounds which can be mixed with the compounds of the invention are: 1,4-bis-(benzoxazol-2'-yl)-naphthalene, 4,4'-bis-(ethoxycarbonylvinyl)-stilbene, 4,4'-bis-(cyanovinyl)-stilbene, 1,4-bis(2'-cyanostyryl)-benzene, 1,5-bis-(benzoxazole-2'-yl)-thiophene, 1-phenyl-4-(5',7'-dimethylbenzoxazol-2'-yl)-stilbene, 1,2-bis-(5'-methylbenzoxazol-2'-yl)-vinylene, 4-(benzoxazol-2'-yl)-4'-(3''-methyl-1'',2'',4''-oxadiazol-5''-yl)-stilbene and 2,4-dimethoxytriazine-6-yl-pyrene.

These compounds are advantageously mixed with compounds of the formula

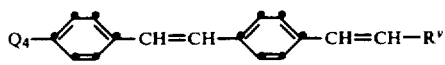

$$Q_4-\underset{}{\bigcirc}-CH=CH-\underset{}{\bigcirc}-CH=CH-R^v \quad (12)$$

wherein $Q_4$ is a benzoxazol-2-yl radical, a pyrimidin-2-yl radical, a 4-methylpyrimidin-2-yl radical or a 4,6-dimethylpyrimidine-2-yl radical, and $R^v$ is $C_2$–$C_4$alkoxycarbonyl or cyano.

The fluorescent whitening agent mixtures so obtained contain the compound of the invention and the known compound in the ratio of 1:9 to 9:1, preferably 1:2 or 2:1.

If the whitening process is combined with textile treatment or finishing methods, the combined treatment can in many cases advantageously be carried out with the aid of appropriate stable preparations which contain the fluorescent whitener compounds in a concentration such that the desired white effect is achieved.

In certain cases, the fluorescent whitening agents are made fully effective by an aftertreatment. This can be, for example, a chemical treatment (for example acid treatment), a thermal treatment or a combined chemical/thermal treatment. Thus, for example, the appropriate procedure to follow in whitening a number of fibre substrates, for example polyester fibres, with the fluorescent whitening agents of the present invention, is to impregnate these fibres with the aqueous dispersions (or optionally also solutions) of the whitening agents at temperatures below 75° C., for example at room temperature, and to subject them to a dry heat treatment at temperatures above 100° C., it being generally advisable additionally to dry the fibrous material beforehand at a moderately elevated temperature, for example in the range from at least 60° C. to about 130° C. The heat treatment in the dry state is then advantageously carried out at a temperature between 120° and 225° C., for example by heating in a drying chamber, by ironing within the specified temperature range or by treatment with dry, superheated steam. The drying and dry heat treatment can also be carried out in immediate succession or be combined in a single procedure.

The amount of fluorescent whitening agent of the present invention to be used, based on the weight of the material to be whitened, can vary within wide limits. A marked and lasting effect can be obtained even with very insignificant amounts, in certain cases 0.0001 percent by weight. But it is also possible to use amounts of up to 0.8 percent by weight and on occasion, up to 2 percent by weight. For most practical purposes, it is preferred to use amounts between 0.0005 and 0.5 percent by weight.

For various reasons it is often advantageous not to use the fluorescent whitening agents by themselves, i.e. pure, but in admixture with a wide variety of assistants and extenders, for example anhydrous sodium sulfate, sodium sulfate decahydrate, sodium chloride, sodium carbonate, alkali metal phosphates, such as sodium or potassium orthophosphate, sodium or potassium pyrophosphate and sodium or potassium tripolyphosphates or alkali metal silicates.

The fluorescent whitening agents of this invention are also particularly suitable for use as additives for wash liquors or heavy duty and domestic detergents, to which they can be added in various ways. They are advantageously added to wash liquors in the form of their solutions in water or organic solvents, or, in dispersed form, as aqueous dispersions. They are advantageously added to domestic or heavy duty detergents in any stage of the production of the detergents, for example to the slurry before the washing powder is atomised, or during the preparation of liquid detergent combinations. They can be added either in the form of a solution or dispersion in water or other solvents or, without assistants, as a dry powder. For example, the whitening agents can be mixed, kneaded or ground with the surface-active substances and, in this form, admixed with the finished powder. However, they can also be sprayed in a dissolved or pre-dispersed form onto the finished detergent.

Suitable detergents are the known mixtures of active detergents, for example soap in the form of chips and powders, synthetics, soluble salts of sulfonic acid hemiesters of higher fatty alcohols, arylsulfonic acids with higher and/or multiple alkyl substituents, sulfocarboxylic acid esters of medium to higher alcohols, fatty acid acylaminoalkyl- or acylaminoaryl-glycerol sulfonates and phosphoric acid esters of fatty alcohols. Suitable builders which can be used are, for example, alkali metal polyphosphates and polymetaphosphates, alkali metal pyrophosphates, alkali metal salts of carboxymethyl cellulose and other soil redeposition inhibitors, and also alkali metal silicates, alkali metal carbonates, alkali metal borates, alkali metal perborates, nitrilotriacetic acid, ethylenediaminetetraacetic acid, and foam stabilisers, such as alkanolamides of higher fatty acids. The detergents can further contain for example: antistatic agents, fat restorative skin protectives, such as lanolin, enzymes, antimicrobial agents, perfumes and colourants.

The novel fluorescent whitening agents have the particular advantage that they are also active in the presence of active chlorine donors, for example, hypochlorite, and can be used without significant loss of effect in wash liquors containing non-ionic washing agents, for example alkylphenolpolyglycol ethers.

The compounds of the invention are added in amounts of 0.005 to 1% or more, based on the weight of the liquid or powdered finished detergent. Wash liquors which contain the indicated amounts of the claimed fluorescent whitening agents impart a brilliant appearance in daylight when used to wash textiles made from cellulose fibres, polyamide fibres, cellulose fibers with a high quality finish, polyester fibers or wool.

The washing treatment is carried out e.g. as follows: The textiles are treated for 1 to 30 minutes at 20° to 100° C. in a wash liquor which contains 1 to 10 g/kg of a built-up composite detergent and 0.05 to 1%, based on the weight of the detergent, of the fluorescent whitening agent. The liquor ratio can be 1:3 to 1:50. After they have been washed, the textiles are rinsed and dried in the usual manner. The wash liquor can contain 0.2 g/l of active chlorine (for example in the form of hypochlorite) or 0.1 go 2 g/l of sodium perborate.

In the following Examples, percentages are always by weight. Unless otherwise stated, melting and boiling points are uncorrected.

EXAMPLE 1

27.5 g of 2-(4-diethoxyphosphorylmethylphenyl)-4,6-dimethoxypyrimidine and 14.3 g of methyl 4-formylcinnamate are dissolved in 150 ml of dimethyl formamide and to this solution are added 4.9 g of sodium methylate, in small portions, in the course of 30 minutes. The reaction mixture is stirred for 30 minutes at room temperature and then for 2½ hours at 40°–45° C. The reaction mixture is cooled to room temperature, acidified with formic acid, and stirred into 800 ml of water and ice. The precipitated product is collected by filtration and dried at 80° C. in vacuo, affording 28 g of the compound of the formula

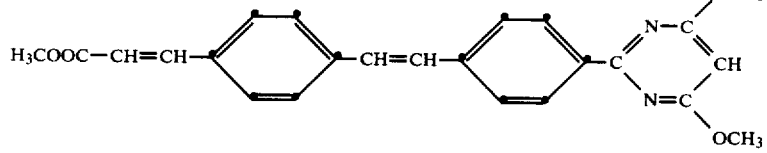

The product crystallises from toluene with the addition of bleaching agents to yellow crystals which have a melting point of 169°–170° C.

The compounds of the formula (102)

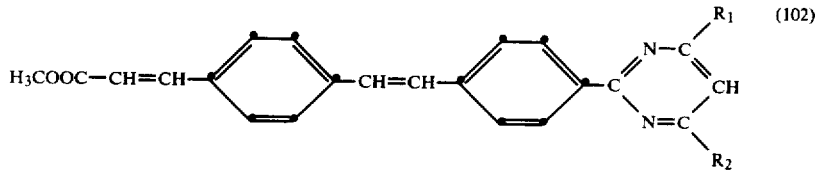

are obtained from the corresponding starting materials listed in Table 1 by repeating the above procedure.

TABLE 1

| Compound | R₁ = R₂ | melting point °C. |
|---|---|---|
| 103 | —OCH₃ | 167–170 |
| 104 | —OC₂H₅ | 192–193 |
| 105 | —OC₃H₇—n | 190–192 |
| 106 | —O-furyl | 216–127 |
| 107 | —SC₂H₅ | 172–173 |
| 108 | —CH₃ | 193–194 |

The 2-(4-bromomethylphenyl)pyrimidines substituted in 4,6-position and required as starting materials for the synthesis of the phosphonates are prepared in the following manner: 102.3 g of p-tolylamidine hydrochloride and 99.3 g of diethyl malonate are suspended in 520 ml of anhydrous ethanol. With efficient stirring and cooling, 323.7 g of a 30% sodium methylate solution is introduced. The reaction mixture is then heated to reflux and stirred for 4 to 5 hours under reflux. The solvent is distilled off and the residue is taken up in 1000 ml of water. After heating to 80° C., the somewhat turbid solution is filtered over silica gel. After cooling and acidifying with 15% hydrochloric acid, the dense crystal slurry is filtered and the filter cake is washed with water and dried at 100° C., affording 100 to 110 g of the compound of the formula

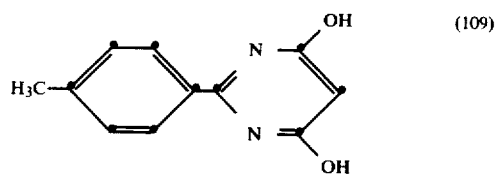

The product has a melting point of 314° C. (with decomposition). 72.6 g of the above dihydroxy compound, 72.6 g of N,N-dimethyl aniline and 363 g of phosphoroxy chloride are heated to the boil and stirred for 1 hour under reflux. Excess phosphoroxy chloride is distilled off and the residual product is washed with ice-water to remove phosphoroxy chloride still adhering to it. The product is then triturated with ice-water, washed with ice-water and dried in vacuo at 40°–50° C., affording 85.9 g of the compound of the formula

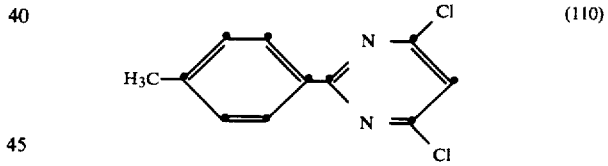

with a melting point of 86°–87° C. 156.1 g of a 30% sodium methylate solution are stirred with 700 ml of anhydrous methanol. While cooling gently, 95.64 g of the compound of the formula (110) are added to the solution in the course of 10 minutes. The reaction mixture is then heated to reflux and kept for 4 hours at the boil. The solvent is distilled off and the residue is poured into 1000 ml of water. Sodium chloride that has formed is removed by trituration with water. The product is collected by filtration, washed with water and dried in the air, affording 90.4 g of the compound of the formula

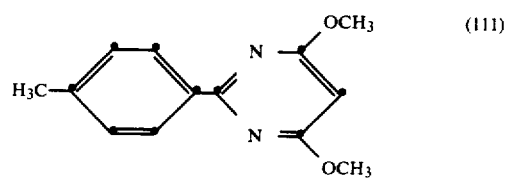

with a melting point of 61°–62° C.

The pyrimidines of the formula

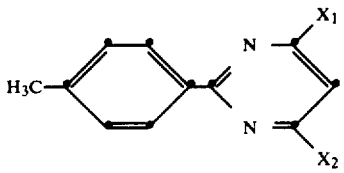 (112)

listed in Table III are obtained in similar manner:

TABLE II

| Compound | $X_1$ | $X_2$ | melting point °C. |
|---|---|---|---|
| 113 | —OC$_2$H$_5$ | —OC$_2$H$_5$ | 71-71 |
| 114 | —OCH(CH$_3$)$_2$ | —OCH(CH$_3$)$_2$ | b.p. 123 5.332 Pa |
| 115 | —O-furfuryl | —O-furfuryl | 125-126 |
| 116 | —OCH$_2$—CH$_2$—OCH$_3$ | —OCH$_2$—CH$_2$—OCH$_3$ | pale yellow oil |
| 117 | —N(morpholino) | —N(morpholino) | 186-187 |
| 118 | —NH—CH$_3$ | —OCH$_2$—CH$_2$—OCH$_3$ | 65-66 |
| 119 | —N(C$_2$H$_5$)$_2$ | —OCH$_2$—CH$_2$—OCH$_3$ | pale yellow oil |
| 120 | —NH—CH$_3$ | Cl | 107 |
| 121 | —N(C$_2$H$_5$)$_2$ | Cl | 74-75 |
| 122 | —OC$_3$H$_7$ | —OC$_3$H$_7$ | 62 |
| 123 | —SC$_2$H$_5$ | —SC$_2$H$_5$ | 55-56 |
| 124 | —OC$_4$H$_9$ | —OC$_4$H$_9$ | b.p. 158-161 13.332 Pa |

115.2 g of 4,6-dimethoxy-2-(4-methylphenyl)pyrimidine in 500 ml of tetrachloromethane are heated to 70° C. To this solution is added, at 70°-75° C., a mixture of 0.5 g of dibenzoyl peroxide, 1 g of azoisobutyronitrile and 90.8 g of N-bromosuccinimide in the course of 30 minutes, while simultaneously irradiating with a 500 watt lamp. The reaction is brought to completion by heating the reaction mixture to reflux for a further 2½ hours. The succinimide is removed by filtration at 65° C. and the filtrate is evaporated to dryness, affording 144 g of crude product of the formula

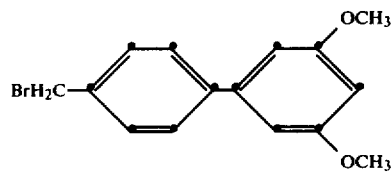 (125)

The product can be purified by recrystallisation from ethanol/ethylene glycol monomethyl ester (1:1). It has a melting point of 132°-134° C.

The bromomethyl compounds of the formula

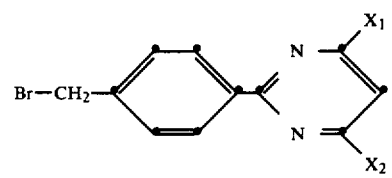 (126)

listed in Table III are obtained in similar manner:

TABLE III

| Compound | $X_1$ | $X_2$ | melting point °C. |
|---|---|---|---|
| 127 | —OC$_2$H$_5$ | —OC$_2$H$_5$ | 95-96 |
| 128 | —OC$_3$H$_7$ | —OC$_3$H$_7$ | 68-70 |
| 129 | —O-furfuryl | —O-furfuryl | 134-136 |
| 130 | —CH$_3$ | —CH$_3$ | 156-157 |
| 131 | —SC$_2$H$_5$ | —SC$_2$H$_5$ | yellow oil |
| 132 | —OC$_4$H$_9$ | —OC$_4$H$_9$ | pale yellow oil |

116.4 g of 2-(4-bromomethylphenyl)-4,6-dimethoxypyrimidine and 400 ml of triethylphosphite are heated to 150°-155° C. in the course of 2½ hours, and the mixture is stirred for a further 3½ hours at the same temperature. Excess triethylphosphite is then distilled off, leaving as residue 128 g of a pale yellow oil (boiling point: 207°-210° C./13.332 Pa) which crystallises out. The colourless crystals obtained have a melting point of 74°-76° C.

The following phosphonates of the formula

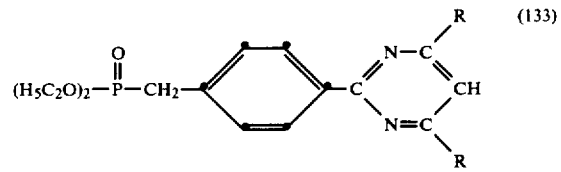 (133)

are obtained in similar manner.

TABLE IV

| Compound | R | melting point °C. |
|---|---|---|
| 134 | —CH$_3$ | 67-69 |
| 135 | —OC$_2$H$_5$ | pale yellow oil |
| 136 | —OC$_3$H$_7$ | 77-79 |
| 137 | —O-furfuryl | colourless semi-crystalline product |
| 138 | —SC$_2$H$_5$ | pale yellow oil |

TABLE IV-continued

| Compound | R | melting point °C. |
|---|---|---|
| 139 | —OC₄H₉ | pale yellow oil | at the boil until hydrogen chloride has ceased to evolve. The solvent is distilled off and the residue is washed first with methanol and then recrystallised from cyclohexane in the presence of fuller's earth, affording 8.2 g of the compound of the formula

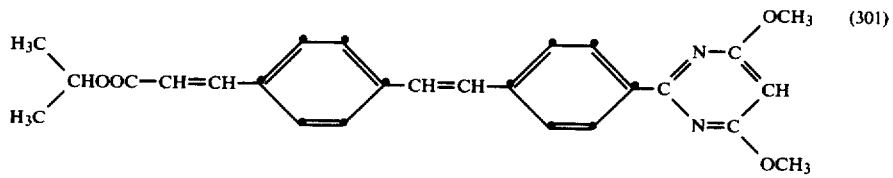

with a melting point of 126°-127° C.

EXAMPLE 2

36.63 g of 2-(4-diethoxyphosphorylmethylphenyl)-4,6-dimethoxypyrimidine and 17.62 g of 4-formylcinnamic acid are heated to 40°-45° C. in 220 ml of dimethyl formamide. Into this solution are then introduced 35.4 g of a 30.5% sodium methylate solution in the course of 20 minutes. The dense slurry of the reaction product is stirred for 3 hours at 40°-45° C., then cooled to room temperature and diluted with 500 ml of water. After acidification with 15% hydrochloric acid, the precipitated product is collected by filtration, washed with water, and dried in vacuo at 80° C., affording 36.4 g of the compound of the formula

EXAMPLE 4

16.1 g of the compound of the formula (101) obtained in Example 1 are heated to 110° C. in 130 ml of ethylene glycol monomethyl ether. A trace of lithium amide is then added to the solution. The mixture is heated to reflux and refluxed for 1½ hours. The solvent is distilled off and the product is treated with methanol, collected by filtration, washed and dried, affording 14.9 g of the compound of the formula

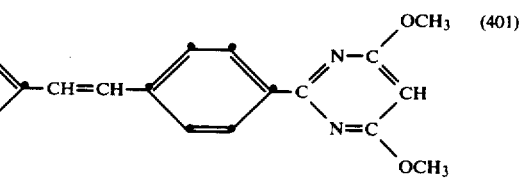

The product crystallises from a mixture of cyclohexane/toluene or from tetrachloroethylene. The yellow crystals obtained have a melting point of 110°-111° C.

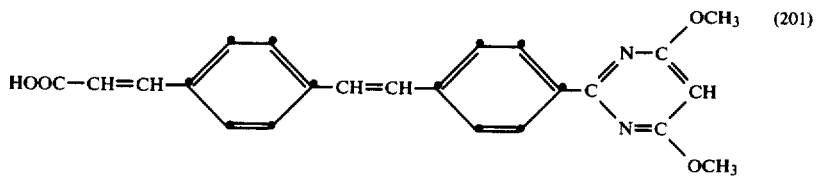

The product crystallises from a small amount of dimethyl formamide. The yellow crystals obtained have a melting point of 278°-279° C.

EXAMPLE 3

13.6 g of the acid of formula (201) are heated to 70°-75° C. in 120 ml of toluene and a small amount of dimethyl formamide. Then 3.5 ml of thionyl chloride are added to the suspension in the course of 15 minutes. The solution obtained is heated to the boil until the evolution of hydrogen chloride has ceased. Then 30 ml of toluene and excess thionyl chloride are distilled off. After cooling to 80° C., 50 ml of isopropanol are added to the solution. The mixture is again heated to and kept

EXAMPLE 5

13.5 g of 1-methyl-3-(4-diethoxyphosphorylmethylphenyl)-pyridazinone and 7.6 g of methyl 4-formylcinnamate are dissolved in 100 ml of dimethyl formamide. To the solution are then added 2.6 g of solid sodium methylate in the course of 10 minutes. The reaction mixture is stirred for 20 minutes at room temperature and then heated to 40°-45° C. for 2 hours. The reaction mixture is then stirred into 800 ml of water. After acidification with formic acid, the product is collected by filtration, washed with water and with methanol and dried in vacuo at 80° C., affording 10.9 g of the compound of the formula

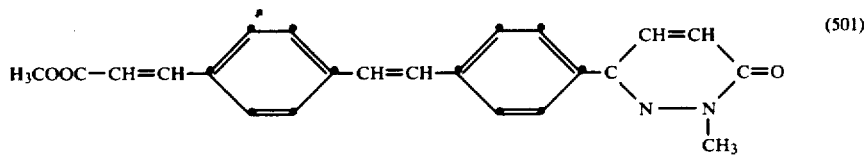
(501)

The product crystallises from a mixture of o-dichlorobenzene/chlorobenzene in the ratio 1:1. The yellow crystals obtained have a melting point of 248°–250° C.

The 1-methyl-3-(4-diethoxyphosphorylmethyl-phenyl)pyridazinone used as starting material is prepared as follows:

110 g of 1-methyl-3-(4-methylphenyl)pyridazinone and 700 ml of tetrachloromethane are heated to 70° C. To the resultant solution is then added, in the course of 40 minutes and at 70°–75° C., a mixture of 3.5 g of dibenzoyl peroxide and 103.3 g of N-bromosuccinimide, while simultaneously irradiating with a 500 watt lamp. The reaction mixture is subsequently stirred for a further 3 hours at reflux temperature. The succinimide is then isolated by filtration at 65° C. and the filter cake is washed with 100 ml of hot tetrachloromethane. The filtrate is evaporated to dryness and the residue is stirred, while still warm, with 100 ml of methanol, whereupon the product crystallises. After cooling, the product is collected by filtration, washed with a small amount of cold methanol, and dried in vacuo at 80° C., affording 115.2 g of the compound of the formula

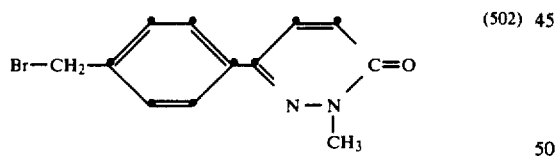
(502)

which crystallises from methanol. The colourless crystals obtained have a melting point of 135°–136° C.

The 1-methyl-3-(4-diethoxyphosphorylmethyl-phenyl)pyridazinone of the formula (503)

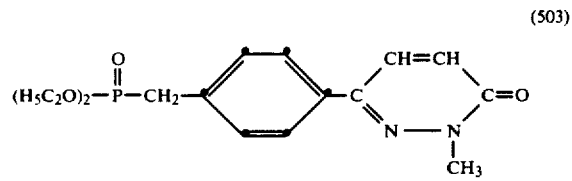

is obtained by reacting 1-methyl-3-(4-bromomethyl-phenyl)-pyridazinone with triethylphosphite as described in Example 1. The colourless crystals obtained have a melting point of 91°–92° C.

EXAMPLE 6

The compound of the formula

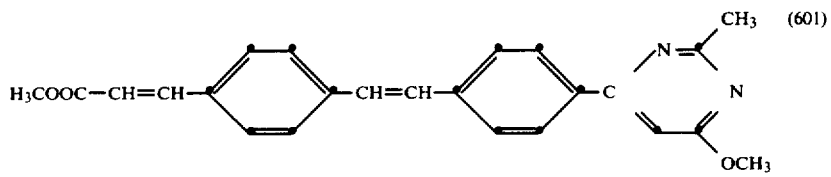
(601)

(m.p. 240°–241° C.) is obtained in a manner similar to that described in Example 5 by reacting 2-methyl-4-methoxy-6-(4-diethoxyphosphorylmethylphenyl)-pyrimidine with 4-formylcinnamic acid.

The 2-methyl-4-methoxy-6-(4-diethoxyphosphoryl-methylphenyl)-pyrimidine required for the synthesis is obtained as described in Example 1 by reacting 2-methyl-4-methoxy-6-(4-bromomethylphenyl)pyrimidine with triethylphosphite. It is obtained in the form of colourless crystals with a melting point of 82°–83° C.

The 2-methyl-4-methoxy-6-(4-bromomethylphenyl)-pyrimidine is prepared as follows: 70.9 g of acetamidine hydrochloride and 154.65 g of p.tolylacetoacetate are heated to 60° C. in 450 ml of anhydrous methanol. At this temperature, 265.6 g of a 30.5% sodium methylate solution is introduced in the course of 1 hour. The resultant suspension is refluxed for a further 3 hours. After cooling, the reaction mixture is stirred into 150 ml of ice and water to form a yellow solution. This solution is acidified with 45 ml of glacial acetic acid, whereupon a dense crystal slurry forms. The crystals are collected by filtration, washed free of acid with water and dried in vacuo at 70°–80° C., affording 95 g of crude product of the formula

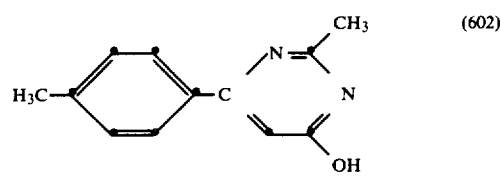
(602)

The compound can be purified by recrystallisation from chlorobenzene and has a melting point of 278°–279° C. While cooling and with efficient stirring, 76 g of the above 2-methyl-4-hydroxy-6-(p-tolyl)-pyrimidine are added in the course of 10 minutes to a mixture consisting of 171 g of phosphoroxy chloride and 19 g of triethylamine. The dense slurry obtained is heated in the course of 30 minutes to 100°–105° C. to form a solution, which is stirred for 1 hour at the same temperature. After cooling to 50° C., the reaction solution is rapidly stirred into a mixture of 1000 ml of water and ice. The precipitated product is stirred ice-cold for 20 minutes, then collected by filtration, washed with ice-cold water and dried in the air, affording 86.5 g of crude product of the formula

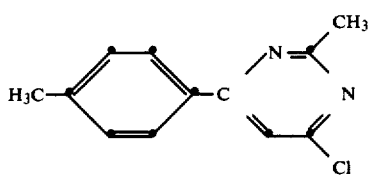

The product is purified by dissolving it in 400 ml of hexane, removing a small amount of undissolved brown by-product and concentrating the yellow hexane solution in vacuo. The yellow oil obtained solidifies on cooling to form pale yellow crystals. Yield: 81 g.

76.51 g of the crude product are added, without further purification, to 350 ml of anhydrous methanol containing 69.3 g of a 30% sodium methylate solution. The reaction mixture is heated to reflux and stirred for 4 hours at reflux temperature, then evaporated to dryness. The resultant crystal slurry is treated with 1000 ml of ice-water and the product is collected by filtration, washed with water and dried at 40°–45° C. in vacuo. Yield: 75.1 g of crude product of the formula (604)

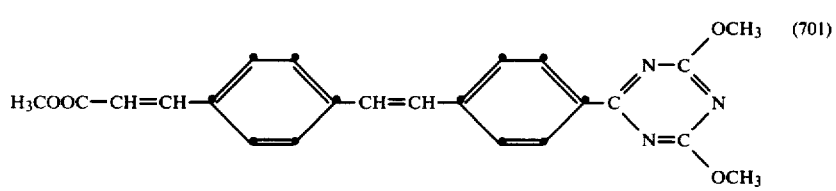

which crystallises from methanol. The colourless crystals obtained have a melting point of 78°–79° C.

The product is then brominated in the side-chain with N-bromosuccinimide as described in Example 1 (melting point of the 2-methyl-4-methoxy-6-(4-bromomethylphenyl)pyrimidine: 93°–94° C.).

EXAMPLE 7

The compound of the formula

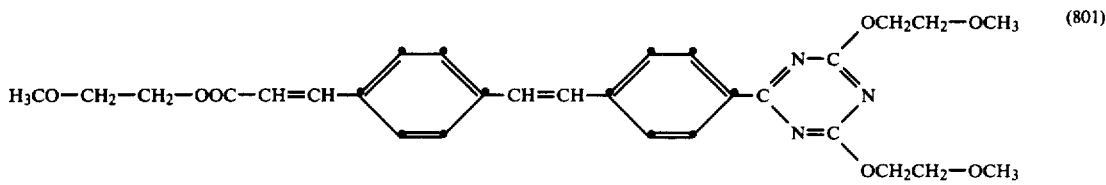

(m.p. 201°–202° C.) is obtained in the same manner by reacting methyl 4-formylcinnamate with 2,4-dimethoxy-6-(4-dimethoxyphosphorylmethylphenyl)-1,3,5-triazine.

EXAMPLE 8

8.06 g of the compound of the formula (701), 150 ml of ethylene glycol monomethyl ether and 0.1 g of lithium amide are refluxed for 1½ hours. The solvent is evaporated off, affording 7.4 g of the compound of the formula

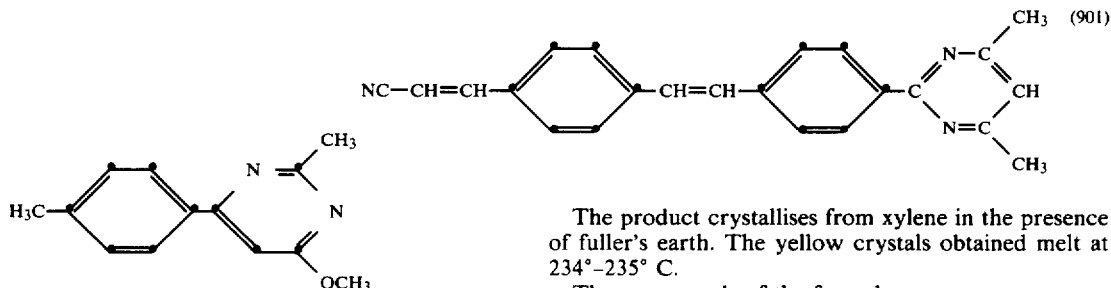

The product crystallises from a mixture of toluene/cyclohexane (1:1) in the presence of fuller's earth. The yellow crystals obtained melt at 103°–104° C.

EXAMPLE 9

13.4 g of 2-(4-diethoxyphosphorylmethylphenyl)-4,6-dimethylpyrimidine and 6.3 g of 4-formylcinnamonitrile are dissolved in 100 ml of dimethyl formamide. Then 2.58 g of sodium methylate are added to the solution in the course of 15 minutes. The reaction mixture is stirred for 1 hour at room temperature and then for 2 hours at 40°–45° C. The reaction mixture is then poured into 800 ml of ice-water, acidified with formic acid, and filtered. The filter cake is washed with water and methanol and dried, affording 10.8 g of the compound of the formula

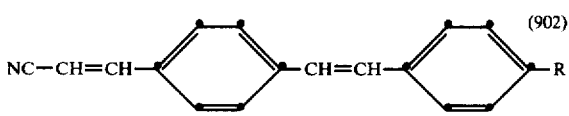

The product crystallises from xylene in the presence of fuller's earth. The yellow crystals obtained melt at 234°–235° C.

The compounds of the formula (902)

NC—CH=CH—⟨⟩—CH=CH—⟨⟩—R listed in Table V are obtained from the corresponding starting materials in similar manner:

TABLE V

| Compound | R | melting point °C. |
|---|---|---|
| 903 | (pyrimidine with OCH₃, OCH₃) | 218–219 |
| 904 | (pyrimidine with OC₃H₇, OC₃H₇) | 188–189 |
| 905 | (pyrimidine with OC₄H₉, OC₄H₉) | 161–162 |
| 906 | (pyrimidine with OCH₃, OCH₃) | 266–267 |
| 907 | (pyrazolone with CH=CH, C=O, CH₃) | 209–211 |
| 908 | (pyrimidine with OCH₃, OCH₃) | 226–227 |
| 909 | (pyrazine ring N—CH, N=CH) | |

EXAMPLE 10

13.13 g of 4,6-dichloro-2-(4-diethoxyphosphorylmethylphenyl)pyrimidine and 5.5 g of 4-formylcinnamonitrile are dissolved in 100 ml of dimethyl formamide. To this solution is then added, in the course of 25 minutes, a solution of 3.4 g of sodium in 65 ml of ethylene glycol monomethyl ether. The reaction mixture is heated to 40° C., stirred for 2 hours at this temperature, then stirred into 800 ml of ice and water. After acidification with formic acid, the precipitate is collected by filtration, washed and dried, affording 15.4 g of the compound of the formula

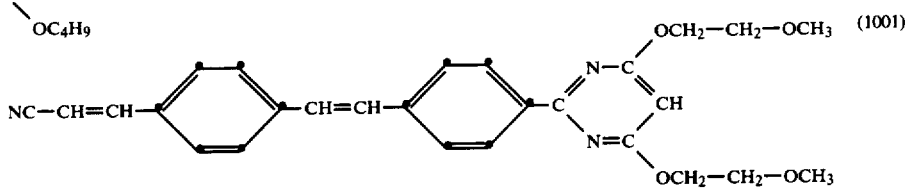
(1001)

The compound is purified by column chromatography over silica gel (solvent and eluant toluene/ethyl acetate 80:20), affording 8.2 g of the compound of the formula (1001) with a melting point of 141°–142° C.

The 4,6-dichloro-2-(4-diethoxyphosphorylmethylphenyl)pyrimidine (m.p. 111°–112° C.) required for the synthesis is obtained by reacting 4,6-dichloro-2-(bromomethylphenyl)pyrimidine (m.p. 155°–156° C.) with triethylphosphite.

EXAMPLE 11

13.7 g of 2-[(4-dibutoxyphosphorylmethyl)phenyl]-5-(p-tolyl)-1,3,4-oxadiazole, 5.7 g of methyl 4-formylcinnamate and 80 ml of dimethyl formamide are treated with 1.95 g of sodium methylate at room temperature in the course of 10 minutes. The suspension is stirred for 30 minutes at room temperature and then for 2½ hours at 40°–45° C. After acidification with formic acid, the suspension is poured into 750 ml of water and ice. The precipitated product is collected by filtration, washed with water and methanol and dried, affording 8.3 g of the compound of the formula

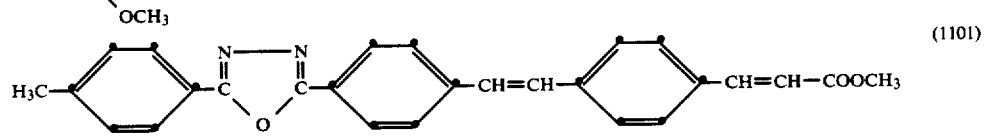
(1101)

The product crystallises from a mixture of xylene and chlorobenzene (4:6) in the presence of fuller's earth. The greenish yellow crystals obtained melt at 266°–268° C.

A product of the formula

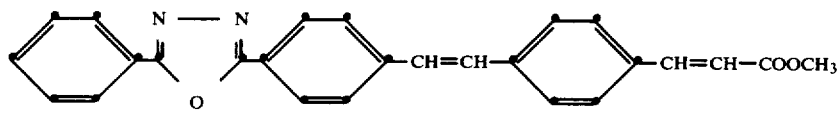
(1102)

(m.p. 227°–228° C.) is obtained by using equimolar amounts of 2-[(4-dibutoxyphosphorylmethyl)phenyl]-5-(phenyl)-1,3,4-oxadiazole instead of 13.7 g of 2-[(4-dibutoxyphosphorylmethyl)phenyl]-5-(p-tolyl)-1,3,4-oxadiazole.

EXAMPLE 12

11 g of a 30% sodium methylate solution are added dropwise at 35° C. in the course of 15 minutes to a solution of 19.4 g of 2-[(4-diethoxyphosphorylmethyl)-phenyl]-4-phenyl-1,3,4-oxadiazol-2-one (cf. European patent specification 9095) and 9.5 g of methyl 4-formylcinnamate in 70 ml of dimethyl formamide, whereupon the temperature rises to 40° C. The reaction mixture is then stirred for 4 hours at 40° C., poured into a mixture of 160 ml of methanol and 250 ml of water, and the aqueous suspension is adjusted with glacial acetic acid to pH 7. The precipitate is filtered with suction, washed with water and dried. Repeated recrystallisation from chlorobenzene with the aid of fuller's earth affords 14.4 g (68% of theory) of the compound of the formula

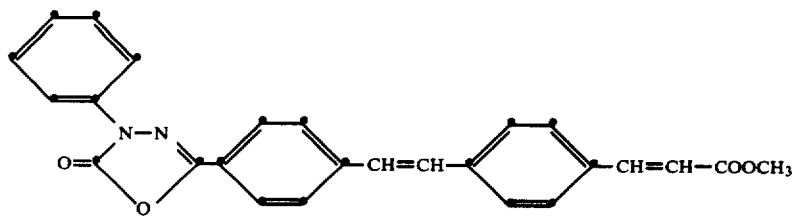
(1201)

in the form of a yellow powder with a melting point of 225°–226° C. The following compound of the formula

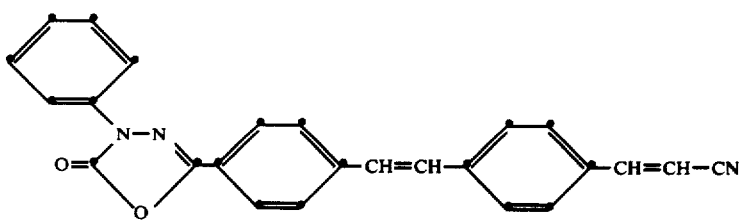
(1202)

(m.p. 237°–238° C.) is also obtained in similar manner using the corresponding starting materials.

EXAMPLE 13

3.3 g of solid sodium methylate are added at room temperature in the course of 10 minutes to a solution of 9.3 g of 3-methyl-1-(4-formylphenyl)pyrazole and 24 g of ethyl 4-(diethoxyphosphorylmethylphenyl)cinnamate in 100 ml of dimethyl formamide, whereupon the temperature rises to 45° C. The reaction mixture is then stirred for 2 hours at 45° C., poured into 500 ml of water, and the aqueous suspension is adjusted with acetic acid to pH 7. The precipitate is filtered with suction and dried. Repeated recrystallisation from chlorobenzene with the aid of fuller's earth affords 9.7 g (54% of theory) of the compound of the formula

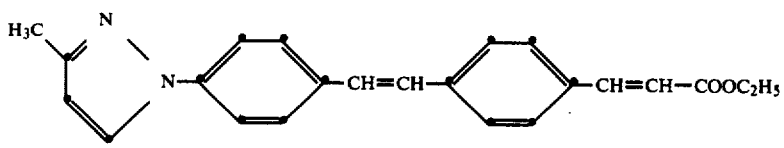
(1301)

in the form of a yellow powder with a melting point of 236°–238° C. The following compound of the formula

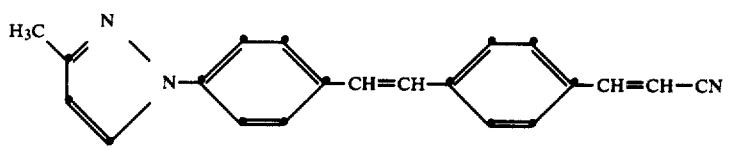
(1302)

is also obtained in similar manner from the corresponding starting materials. Melting point: 249°–250° C. The pyrazole of the formula

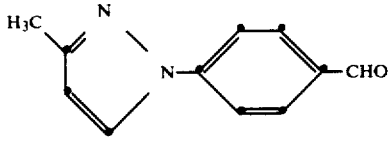

required for the synthesis is obtained as follows:

264 g of 1-acetyl-2,2-dimethoxyethane are added dropwise at room temperature to use a suspension of 465 g of 4-carboxyphenylhydrazine hydrochloride (81%) in 3400 ml of ethanol which contains 253 g of pyridine. The reaction mixture is then kept at reflux temperature for 1 hour. A solution of 73 g of hydrochloric acid in 240 ml of ethanol is then added dropwise. The mixture is stirred for a further 18 hours at 80° C., then a solution of 240 g of sodium hydroxide in 1500 ml of water is added, and the ethanol is distilled off. The precipitated sodium salt of 3-methyl-1-(4-carboxyphenyl)pyrazole is dissolved hot in 1000 ml of water and precipitated with dilute hydrochloric acid. The precipitate is filtered with suction, washed with water and dried. Recrystallisation from methanol affords 361 g (89% of theory) of 3-methyl-1-(4-carboxyphenyl)pyrazole with a melting point of 249°-250° C. A suspension of 101 g of this acid in 500 ml of hexane and 1 ml of dimethyl formamide is heated to 60° C. Then 71 g of thionyl chloride are run into the suspension in the course of 30 minutes. The reaction mixture is stirred for 18 hours at reflux temperature, then 100 ml of toluene are added, and the mixture is again heated to the boil. The clear solution obtained is filtered and, after cooling to 10° C., the precipitated 3-methyl-1-(4-chloroformylphenyl)pyrazole is filtered with suction and dried. Yield: 90 g (82% of theory) in the form of pale crystals which melt at 110°-111° C.

Using the method of Rosenmund, 88 g of the above 3-methyl-1-(4-chloroformylphenyl)pyrazole are hydrogenated with hydrogen at 140° C. in 900 ml of xylene with the addition of 0.23 g of thiourea and 9 g of Pd/BaSO$_4$ (5%). After cooling to 80° C. and removing the catalyst by filtration, the xylene solution is evaporated to dryness and the precipitated product is recrystallised from a mixture of hexane and toluene, affording 68.3 g of 3-methyl-1-(4-formylphenyl)pyrazole in the form of pale yellow crystals with a melting point of 96°-98° C.

88 g of 4-bromomethylcinnamonitrile (obtained by bromination of 4-methylcinnamonitrile with N-bromosuccinimide in carbon tetrachloride, and having a melting point of 105°-107° C.) are mixed with 256 g of triethylphosphite. The mixture is then slowly heated to 150° C. with stirring, and then stirred for 3 hours at this temperature. Excess phosphite is then removed in vacuo, affording the crude phosphonate of the formula

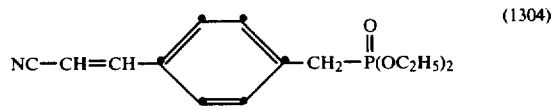

in the form of a light brown oil.

EXAMPLE 14

13.78 g of 1-(4-diethoxyphosphorylmethylphenyl)-3,5-diphenyltriazine and 4.72 g of 4-formylcinnamonitrile are dissolved in 100 ml of dimethyl formamide, and to this solution are added 2.1 g of solid sodium methylate in the course of 15 minutes. The suspension is stirred for 30 minutes at room temperature and stirred for 2 hours at 40°-50° C. to bring the reaction to completion. The reaction mixture is cooled to room temperature, weakly acidified with formic acid, and stirred into 800 ml of ice-water. The precipitated yellow product is collected by filtration, washed with water and methanol and dried at 80° C. in vacuo, affording 12 g of the compound of the formula

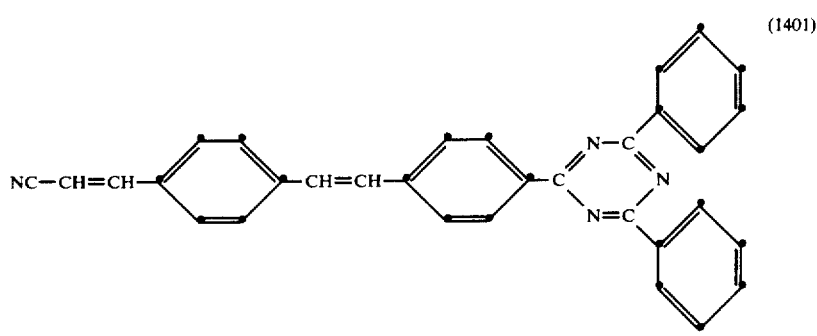

The product crystallises from o-dichlorobenzene with the addition of fuller's earth. The yellow crystals obtained melt at 313°-314° C. The compound of the formula

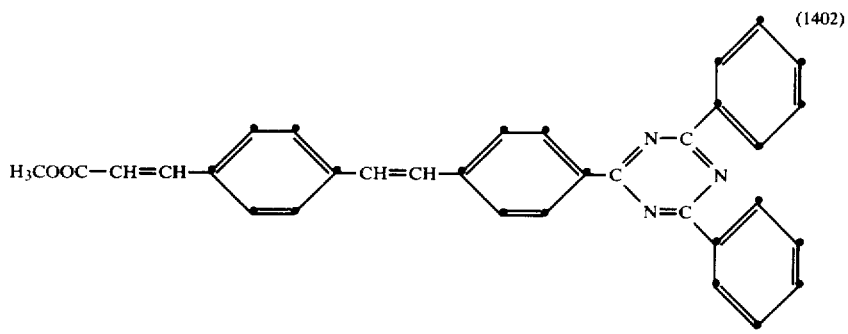

is obtained in similar manner from the corresponding starting materials. It crystallises from xylene in the presence of fuller's earth. The yellow crystals melt at 315°-316° C. The 1-(4-diethoxyphosphorylmethylphenyl)-3,5-diphenyltriazine (m.p. 150°-151° C.) required for the synthesis is prepared as follows:

80.84 g of 1-(p-tolyl)-3,5-diphenyltriazine and 400 ml of ethylene chloride are heated to 75°-80° C. A mixture of 37.87 g of 1,3-dibromo-5,5-dimethylhydantoin and 1 g of azoisobutyronitrile is then added to the above solution in the course of 30 minutes. The reaction mixture is refluxed for 5 hours. The solvent is then removed and the product of the formula

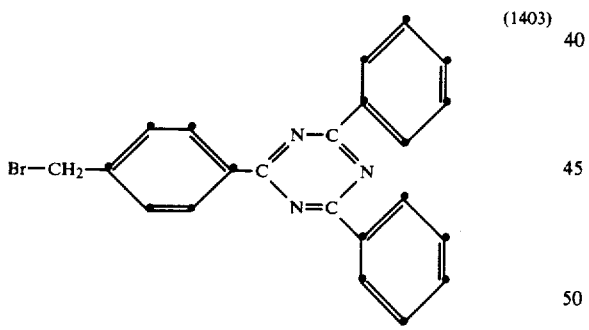

is triturated with water, collected by filtration, washed with water and methanol and dried. Yield: 95.3 g. The product crystallises from ethylene glycol monomethyl ether. The colourless crystals have a melting point of 201°-203° C. 90.5 g of 1-(4-bromomethylphenyl)-3,5-diphenyltriazine and 300 ml of triethylphosphite are heated to 155° C. in the course of 6 hours and the mixture is then stirred for 1 hour at 155° C. Excess triethylphosphite is distilled off and the oily residue is crystallised from petroleum ether. Yield: 107 g. The product crystallises from a small amount of methanol. The colourless crystals have a melting point of 150°-151° C.

EXAMPLE 15

A 30% sodium methylate solution (11 g) is added dropwise at room temperature in the course of 16 minutes to a solution of 17.5 g of 2-(4-diethoxyphosphorylmethylphenyl)-4-methoxy-6-methylpyrimidine and 9.5 g of methyl 4-formylcinnamate in 100 ml of dimethyl formamide, whereupon the temperature rises to 40° C. The reaction mixture is then stirred for 2 hours at 45° C., poured into a mixture of 160 ml of methanol and 250 ml of water, and the aqueous suspension is adjusted to pH 7 with acetic acid. The precipitate is collected by filtration, washed and dried. Repeated recrystallisation from toluene/ligroin (1:1) with the air of fuller's earth yields 12.1 g (62% of theory) of the compound of the formula

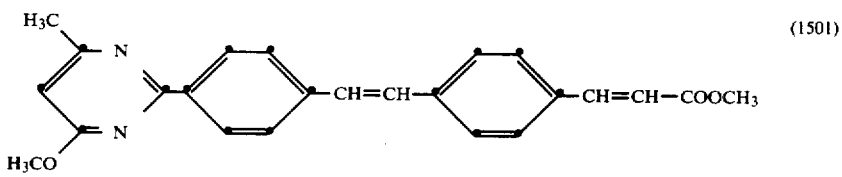

in the form of a yellow powder with a melting point of 175°-176° C.

The compounds of the formula

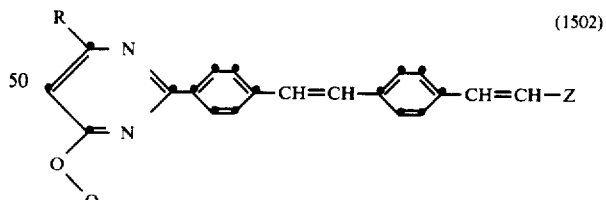

listed in Table VI are obtained in similar manner from the corresponding starting materials:

TABLE VI

| Compound | R | Q | Z | melting point |
|---|---|---|---|---|
| 1503 | CH₃ | C₆H₅ | —COOCH₃ | 182-184 |
| 1504 | C₆H₅ | CH₃ | —COOCH₃ | 179-181 |
| 1505 | C₆H₅ | CH₃ | —CN | 192-194 |
| 1506 | CH₃ | C₆H₅ | —CN | 246-248 |
| 1507 | CH₃ | CH₃ | —CN | 196-197 |

The 2-(4-diethoxyphosphorylmethylphenyl)-4-methoxy-6-methylpyrimidine of the formula

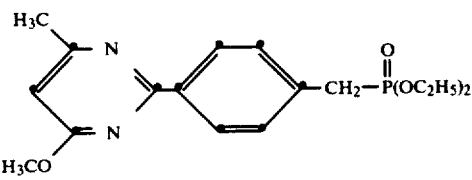
(1508)

is obtained as follows:

A solution of 54 g of sodium methylate in 130 ml of methanol is added dropwise at 60° C. to a solution of 85 g of p-tolylamidine hydrochloride and 80.5 g of ethyl acetoacetate in 250 ml of methanol. The reaction mixture is then refluxed for 4 hours, poured into 1000 ml of water, and adjusted to pH 6–7 with acetic acid. The precipitate is collected by filtration, washed with water and dried, affording 94.4 g (94% of theory) of 4-hydroxy-6-methyl-2-p-tolylpyrimidine with a melting point of 206°–207° C.

4-Hydroxy-6-phenyl-2-p-tolylpyrimidine with a melting point of 282°–283° C. is obtained by using an equivalent amount of ethyl benzoylacetate instead of 80.5 g of ethyl acetoacetate and repeating the above procedure.

183 g of phosphoroxy chloride are put into a reaction vessel at 5° C. and, at this temperature, 20 g of triethylamine are added dropwise. To this mixture are then added 80 g of 4-hydroxy-6-methyl-2-p-tolylpyrimidine at 10°–15° C. The reaction mixture is then heated within 30 minutes to 100° C., stirred for 1 hour at this temperature, cooled, and poured into ice-water. The precipitate is collected by filtration, washed neutral and dried, affording 85.5 g (98% of theory) of 4-chloro-6-methyl-2-p-tolylpyrimidine with a melting point of 103°–104° C.

4-Chloro-6-phenyl-2-p-tolylpyrimidine with a melting point of 86°–87° C. is obtained by using an equivalent amount of 4-hydroxy-6-phenyl-2-p-tolylpyrimidine instead of 80 g of 4-hydroxy-6-methyl-2-p-tolylpyrimidine and repeating the above procedure.

A solution of 11.5 g of sodium in 100 ml of methanol is added to a suspension of 76.5 g of 4-chloro-6-methyl-2-p-tolylpyrimidine in 200 ml of methanol. The reaction mixture is refluxed for 2 hours and poured into water. The precipitate is filtered with suction, washed with water and dried, affording 72.9 g (97% of theory) of 4-methoxy-6-methyl-2-p-tolylpyrimidine with a melting point of 66°–67° C.

4-Methoxy-6-phenyl-2-p-tolylpyrimidine with a melting point of 99°–100° C. is obtained by using an equivalent amount of 4-chloro-6-phenyl-2-p-tolylpyrimidine instead of 76 g of 4-chloro-6-methyl-2-p-tolylpyrimidine and repeating the above procedure.

A mixture of 9.4 g of N-bromosuccinimide and 0.2 g of azoisobutyronitrile is added in portions at 70° C. and in the course of 30 minutes to a solution of 10.7 g of 4-methoxy-6-methyl-2-p-tolylpyrimidine and 0.2 g of dibenzoyl peroxide in 100 ml of anhydrous tetrachloromethane. The mixture is then kept for 2 hours at reflux temperature. After cooling, the succinimide is filtered with suction and the filter cake is washed with 200 ml of tetrachloromethane and the filtrate is concentrated. Recrystallisation from n-hexane affords 11 g (75% of theory) of 2-(4-bromomethylphenyl)-4-methoxy-6-methylpyrimidine with a melting point of 98°–99° C.

2-(4-Bromomethylphenyl)-4-methoxy-6-phenylpyrimidine with a melting point of 98°–100° C. is obtained by using an equivalent amount of 4-methoxy-6-phenyl-2-p-tolylpyrimidine instead of 10.7 g of 4-methoxy-6-methyl-2-p-tolylpyrimidine and repeating the above procedure.

A mixture consisting of 250 g of 2-(4-bromomethylphenyl)-4-methoxy-6-methylpyrimidine and 540 g of triethylphosphite is slowly heated to 150° C. with stirring, and then stirred for 5 hours at this temperature. Excess triethylphosphite is then removed in vacuo, affording the crude phosphate in the form of a light brown oil. The phosphate of the formula

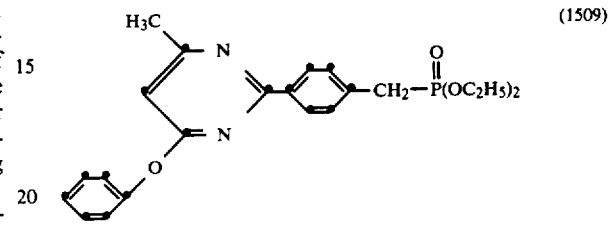
(1509)

is obtained in similar manner in the form of a light brown oil.

The 2-p-tolyl-4-methyl-6-phenoxypyrimidine required for the synthesis is obtained as follows:

A mixture of 250 g of phenol and 29.7 g of sodium methylate is heated to an interval temperature of 160° C. while simultaneously distilling off methanol. The melt obtained is cooled to 120° C., then 109 g of 4-chloro-6-methyl-2-p-tolylpyrimidine are added and the mixture is stirred for 3 hours at 120° C. After cooling, excess phenol is removed with steam, and the residue is filtered with suction, washed with water and dried. Recrystallisation from methanol yields 119.4 g (86.5% of theory) of 4-methyl-6-phenoxy-2-p-tolylpyrimidine with a melting point of 90°–91° C.

The preparation of 2-(4-bromomethylphenyl)-4-methyl-6-phenoxypyrimidine with a melting point of 126°–127° C. is effected as described above with N-bromosuccinimide in 76% yield. The preparation of 2-(4-diethoxyphosphorylmethylphenyl)-4-methoxy-6-phenoxypyrimidine is likewise effected in similar manner.

The diethoxyphosphorylmethyl compound of the formula

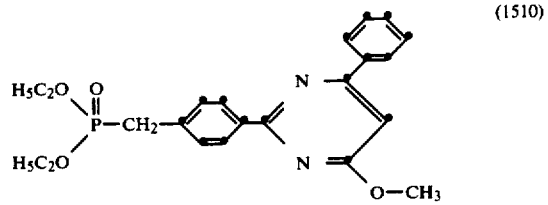
(1510)

is obtained as follows:

With stirring, a mixture of 89 g of 2-(4-bromomethylphenyl)-4-methoxy-6-phenylpyrimidine and 166 g of triethylphosphite is slowly heated to 150° C., and then stirred for 5 hours at this temperature. The bulk of excess triethylphosphite is subsequently distilled off in vacuo, and the residue is chromatographed over silica gel. Yield: 79.3 g (77% of theory) in the form of colourless crystals which melt at 73°–75° C.

EXAMPLE 16

A 30% sodium methylate solution (11 g) is added dropwise at room temperature in the course of 15 minutes to a solution of 16 g of 2-(4-diethoxyphosphorylmethylphenyl)-4-methylpyrimidine and 7.85 g of 4-formylcinnamonitrile in 100 ml of dimethyl formamide, whereupon the temperature rises to 40° C. The reaction mixture is then stirred for 4 hours at 45° C., poured into a mixture of 160 ml of methanol and 250 ml of water, and the aqueous suspension is adjusted with acetic acid to pH 7. The precipitate is filtered with suction, washed with water and dried. Repeated recrystallisation from toluene with the aid of fuller's earth yields 10.2 g (63% of theory) of the compound of the formula

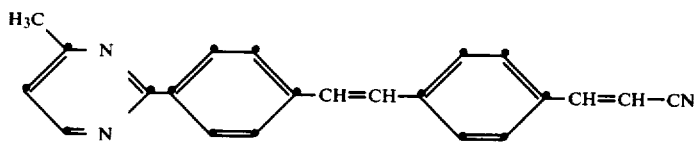
(1601)

in the form of a yellow powder with a melting point of 246°-248° C.

The following compound of the formula

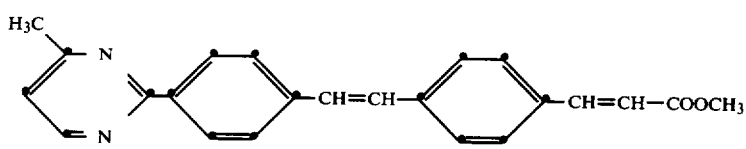
(1602)

with a melting point of 207°-208° C. is also obtained in similar manner from the corresponding starting materials. The phosphonate of the formula (1603)

employed is obtained as follows:

A solution of 108 g of sodium methylate in 260 ml of methanol is added dropwise at 50° C. to a solution of 170 g of p-tolylamidine hydrochloride and 150 g of 1-acetyl-2,2-dimethoxyethane in 500 ml of methanol. The reaction mixture is then stirred for 4 hours at 50° C., poured into 2000 ml of water, and adjusted to pH 7 with acetic acid. The precipitate is filtered with suction, washed with water and dried, affording 167 g (91% of theory) of 2-(4-methylphenyl)-4-methylpyrimidine with a melting point of 80°-81° C.

Reaction of this 2-(4-methylphenyl)-4-methylpyrimidine with N-bromosuccinimide, as described in Example 15, affords 2-(4-bromomethylphenyl)-4-methylpyrimidine with a melting point of 104°-106° C. after recrystallisation from ligroin. A mixture of 105 g of 2-(4-bromomethylphenyl)-4-methylpyrimidine and 265 g of triethylphosphite is slowly heated, with stirring, to 150° C., while simultaneously distilling off ethyl bromide, and then stirred for 5 hours at this temperature. After distilling off excess triethylphosphite, the phosphate is obtained in a yield of 125 g in the form of a light brown viscous oil.

EXAMPLE 17

17.8 g of the compound of the formula (1602) prepared in accordance with Example 16, 80 ml of ethylene glycol monomethyl ether and 0.1 g of lithium amide are heated to 110° C. The solution is then stirred for 6 hours at this temperature. The solvent is distilled off and the product is treated with methanol, collected by filtration, washed with methanol and dried. Repeated recrystallisation from ligroin with the aid of fuller's earth yields 13.9 g (69.4% of theory) of the compound of the formula

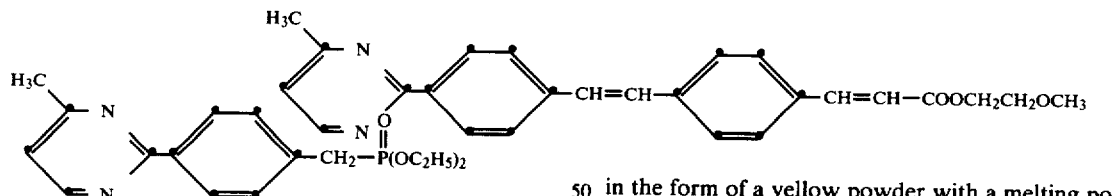
(1701)

in the form of a yellow powder with a melting point of 139°-141° C. The following compounds are also obtained in similar manner from the corresponding starting materials:

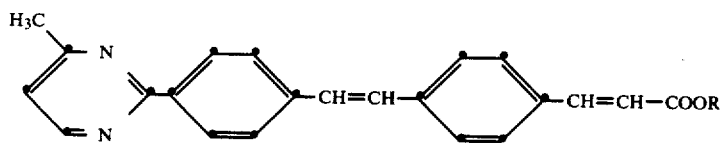
(1702)

| Compound | R | m.p. °C. |
|---|---|---|
| (1703) | —C$_2$H$_5$ | 170–171 |
| (1704) | —C$_3$H$_7$ | 158–160 |
| (1705) | —CH$_2$CH$_2$—O—CH$_2$CH$_3$ | 159–161 |
| (1706) | —CH$_2$CH$_2$—O—CH$_2$CH$_2$—O—CH$_3$ | 149–151 |
| (1707) | —CH$_2$CH$_2$—(OCH$_2$CH$_2$)$_2$—O—CH$_3$ | 114–116 |

-continued

| Compound | R | m.p. °C. |
|---|---|---|
| (1708) | —CH$_2$CH$_2$—CH(CH$_3$)—O—CH$_3$ | 151–153 |
| (1709) | —CH(CH$_3$)—CH$_2$—O—CH$_3$ | 153–156 |
| (1710) | —CH$_2$–(2-furyl methylene dioxy) | 140–142 |
| (1711) | —CH$_2$–(benzodioxole) | 169–171 |

EXAMPLE 18

148 g of terephthaldehyde, 85 g of cyanoacetic acid and 3 g of ammonium acetate are added to 200 ml of toluene and 100 ml of pyridine in a reflux apparatus which is equipped with a Barrett trap for removing water condensed from the reflux vapours. The reaction mixture is heated and, with stirring, kept under moderate reflux until no more water forms (about 2 to 3 hours). After addition of 200 ml of water, the mixture is subjected to steam distillation to remove toluene and other volatile substances. The residue is subsequently stirred vigorously at 50° C. with a solution of 300 g of sodium bisulfite in 900 ml of water, cooled to room temperature and filtered. To the filtrate are added 600 ml of a 30% aqueous formaldehyde solution, and the precipitated aldehyde is taken up in toluene. The toluene solution is dried over magnesium sulfate and, after evaporation of the toluene, the 4-formylcinnamonitrile is distilled. Yield: 84.5 g of the mixture of E-Z isomers with a boiling point of 132°–155° C./13.332 Pa and from which the E-form with a melting point of 118°–119° C. is obtained by crystallisation from methanol.

EXAMPLE 19

With stirring, 6.1 g of 4-(diethoxyphosphorylmethyl)-biphenyl and 4.1 g of methyl 4-formylcinnamate are dissolved at 40° C. in 40 ml of dimethyl formamide. Then 4.25 ml of a 30.7% solution of sodium methylate in methanol are added dropwise, while keeping the temperature below 45° C. by cooling with ice-water. After stirring 2½ hours at 40°–45° C., the suspension is cooled to 10° C., and firstly 67 ml of methanol and then 94 ml of water are added dropwise. After neutralisation with 0.5 ml of 50% acetic acid and cooling to 5° C., the crystallised product is filtered with suction, washed with about 200 ml of methanol/water, and dried in vacuo at 70°–80° C. Recrystallisation from 200 ml of chlorobenzene with the aid of fuller's earth yields 1.5 g of the compound of the formula

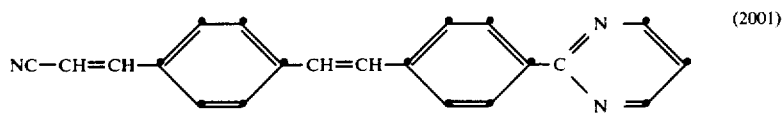
(1901)

in the form of a yellow powder with a melting point of 264°–277° C.

EXAMPLE 20

12.25 g of 2-(4-diethoxyphosphorylmethylphenyl)-pyrimidine and 6.3 g of 4-formylcinnamonitrile are dissolved in 100 ml of dimethyl formamide. To the solution are then added 2.59 g of sodium methylate in the course of 20 minutes. The batch is stirred for 30 minutes at room temperature and then for a further 2½ hours at 40°–41° C. to bring the reaction to completion. The reaction mixture is then poured into 800 ml of ice and water and the aqueous suspension is weakly acidified with formic acid and filtered. The filter cake is washed with water and methanol and dried, affording 9.4 g of the compound of the formula

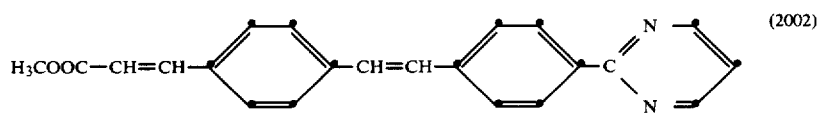
(2001)

The compound crystallises from chlorobenzene in the presence of fuller's earth. The pale greenish-yellow crystals have a melting point of 290°–291° C.

The compound of the formula

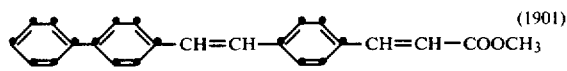
(2002)

with a melting point of 249°–250° C., is obtained in a yield of 9.3 g by using an equivalent amount of methyl 4-formylcinnamate instead of the 6.3 g of 4-formylcinnamonitrile and repeating the same procedure.

13.7 g of the compound of the formula (2002), 200 ml of ethylene glycol monomethyl ether and 0.1 g of lithium amide are refluxed for 4½ hours. After distilling off the solvent, the compound of the formula

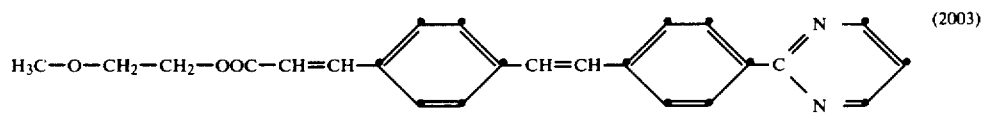
(2003)

which crystallises from xylene, is obtained in a yield of 11.3 g. The greenish yellow crystals have a melting point of 240° C.

The 2-(4-diethoxyphosphorylmethylphenyl)pyrimidine required for the synthesis is prepared as follows:

95.64 g of 2-p-tolyl-4,6-dichloropyrimidine are hydrogenated at room temperature with hydrogen in 1800 ml of anhydrous ethanol with the addition of 72.2 g of solid anhydrous sodium acetate and 10 g of 5% Pd/C. The catalyst is removed by filtration and the ethanolic solution is then evaporated to dryness. The solid product is treated with water and dried, affording 61.9 g of the compound of the formula

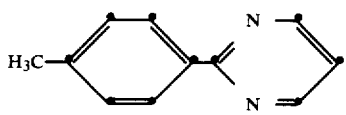
(2004)

in the form of colourless crystals with a melting point of 88°–89° C.

61.3 g of 2-p-tolylpyrimidine are brominated in the side-chain with N-bromosuccinimide as described in Example 1, affording 90.3 g of the compound of the formula

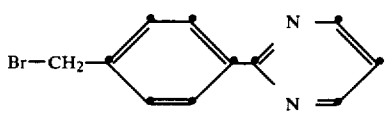
(2005)

which crystallises from methanol. The colourless crystals have a melting point of 103°–104° C.

88.3 g of 2-(4-bromomethylphenyl)pyrimidine of the formula (2005) and 305 ml of triethylphosphite are heated to 145°–150° C. and the mixture is stirred for 4 hours at this temperature. Excess triethylphosphite is distilled off in vacuo, affording 108 g of the compound of the formula

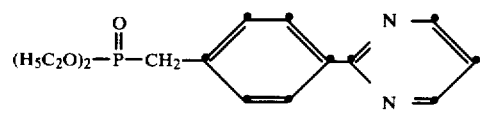
(2006)

in the form of a pale yellow oil, which crystallises after some days.

EXAMPLE 21

12.24 g of 2-(4-diethoxyphosphorylmethylphenyl)-pyrimidine and 6.85 g of 2-methyl-3-(4-formylphenyl)-2-propenonitrile (m.p. 62°–64° C.) are dissolved in 80 ml of dimethyl formamide. To this solution are then added 2.8 g of solid sodium methylate in the course of 10 minutes. The reaction is brought to completion by stirring for a further 2½ hours at 40°–45° C. The mixture is then stirred into 800 ml of ice and water, and the aqueous suspension is acidified with formic acid and filtered. The filter cake is washed with water and methanol and dried, affording 10.7 g of the compound of the formula

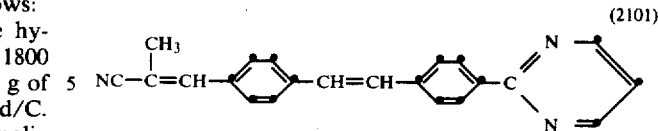
(2101)

The product crystallises from tetrachloroethane in the presence of fuller's earth. The yellow crystals melt at 213°–214° C.

The 2-methyl-3-(4-formylphenyl)-2-propenonitrile used for the synthesis is obtained as follows:

A 30% sodium methylate solution (360 g) is added dropwise at 20°–25° C. to a suspension of 134 g of terephthalaldehyde in 500 ml of methanol. Then 191 g of 2-(diethylphosphoryl)-propionitrile [prepared according to M. L. Raggio and D. S. Watt, J. Org. Chem. 41, 1873 (1976)] are slowly added dropwise to the above reaction solution. The reaction mixture is stirred for 6 hours at room temperature, poured into 1000 ml of water, and the aqueous suspension is adjusted to pH 7 with acetic acid. The precipitated product is dried and then chromatographed over silica gel, affording 35 g (20.5% of theory) of colourless crystals with a melting point of 62°–64° C.

The compound of the formula

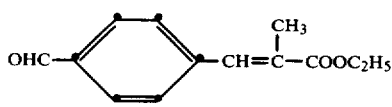
(2102)

with a boiling point of 127°–131° C./7 Pa, is obtained by using an equivalent amount of ethyl 2-(diethylphosphoryl)-propionate instead of 2-(diethylphosphoryl)-propionitrile.

EXAMPLE 22

With stirring, 8.5 g of 2-(4-methylphenyl)pyrimidine and 15 g of methyl 4-(2-chlorophenyliminomethyl)cinnamate are dissolved at 20°–22° C. in 100 ml of dimethyl formamide. Then 5.4 g of sodium methylate are added, whereupon the reaction mixture becomes dark brown and the temperature rises temporarily to 27° C. The reaction mixture is then stirred for 24 hours at 20°–22° C., poured into 400 ml of water, and the yellow precipitate is filtered with suction, washed with water and dried. Chromatography over silica gel yields the compound of the formula

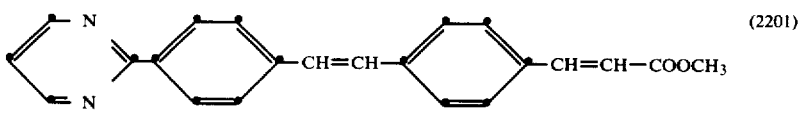
(2201)

with a melting point of 249°–250° C.

The methyl 4-(2-chlorophenyliminomethyl)cinnamate of the formula

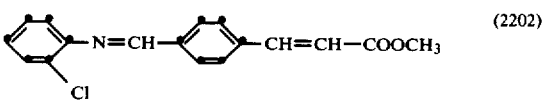
(2202)

is obtained as follows:

14 g of 2-chloroaniline are added at 60° C. to a solution of 19 g of methyl 4-formylcinnamate in 100 ml of methanol, and the yellow solution is stirred for 2 hours under reflux. After cooling to 5° C., the precipitate is filtered with suction, washed with a small amount of methanol and dried at 50° C. Recrystallisation from a mixture of 120 ml of ligroin and 20 ml of toluene yields 22.3 g (74.5% of theory) of the Schiff's base in the form of yellow crystals which melt at 89°-90° C.

EXAMPLE 23

To a solution of 8.8 g of 2-(4'-bromostilben-4-yl)-4-methylpyrimidine, 9.2 g of tri-n-butylamine and 5.3 g of acrylonitrile in 20 ml of toluene are added, at 80° C., 0.6 g of tri-o-tolylphosphine, followed by 0.11 g of palladium acetate. The reaction mixture is then stirred for 4 hours at 90°-95° C., diluted with 20 ml of toluene and cooled to 20° C. The precipitate is collected by filtration, washed with methanol and dried. Recrystallisation from toluene with the aid of fuller's earth yields 2.1 g (26% of theory) of the compound of the formula

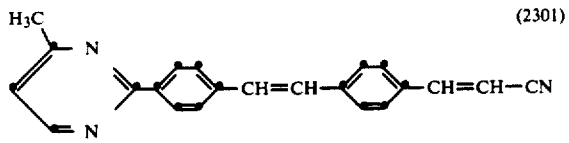
(2301)

in the form of a yellow powder with a melting point of 246°-248° C.

The following compound of the formula

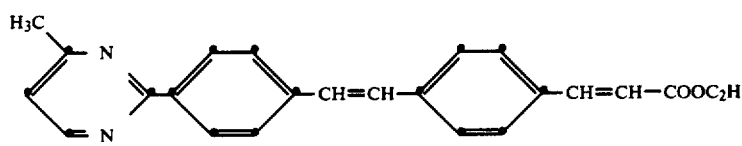
(2302)

with a melting point of 170°-171° C., is obtained by using an equivalent amount of ethyl acrylate instead of 5.3 g of acrylonitrile and repeating the same procedure.

The 2-(4'-bromostilben-4-yl)-4-methylpyrimidine used for the synthesis is obtained as follows:

43.5 g of a 30% sodium methylate solution in methanol are added dropwise at 40° C. to a solution of 69 g of 2-(4-diethoxyphosphorylmethylphenyl)-4-methylpyrimidine and 39 g of 4-bromobenzaldehyde in 100 ml of dimethyl formamide. The reaction mixture is then stirred for 4 hours at 45° C., poured into a mixture of 200 ml of methanol and 200 ml of water, and the aqueous suspension is adjusted to pH 7 with acetic acid. The precipitate is filtered with suction, washed with water and dried. Recrystallisation from a mixture consisting of 250 ml of ligroin and 200 ml of toluene yields 52.2 g (74.5% of theory) of the brominated compound with a melting point of 171°-172° C.

EXAMPLE 24

4.7 g of methyl 4-(diethoxyphosphorylmethyl)-benzoate and 3 g of methyl 4-formylcinnamate are condensed, as described in Example 19, in 30 ml of dimethyl formamide with the addition of 3.4 g of a 30% solution of sodium methylate in methanol. After addition of 50 ml of methanol and 70 ml of water and subsequent neutralisation with 0.4 ml of 50% acetic acid as described, the product is isolated and dried. Recrystallisation from 400 ml of chlorobenzene with the aid of fuller's earth yields 2.3 g of the compound of the formula

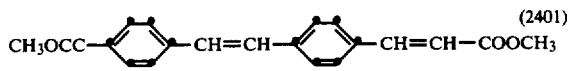
(2401)

in the form of a greenish yellow crystalline powder with a melting point of 226°-227° C.

EXAMPLE 25

5.2 g of the phosphonate of the formula

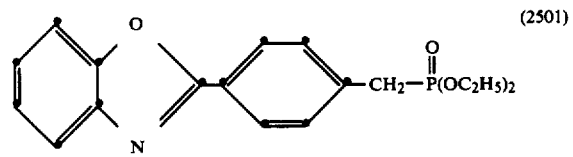
(2501)

and 3 g of methyl 4-formylcinnamate are condensed, as described in Example 19, in 30 ml of dimethyl formamide with the addition of 3.2 ml of a 30% solution of sodium methylate in methanol. The product is isolated and recrystallised twice from 300 ml of chlorobenzene, affording 3 g of the compound of the formula

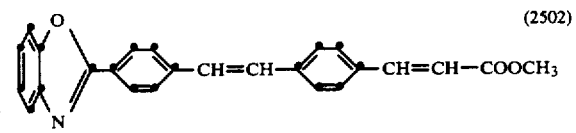
(2502)

in the form of a pale yellow greenish crystalline powder with a melting point of 244°-245° C.

The compounds of the formula

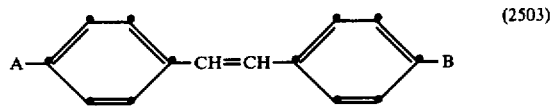
(2503)

are obtained by procedures similar to those described in the preceding Examples:

TABLE VII
| Compound | A | B | melting point °C. |
|---|---|---|---|
| (2504) | 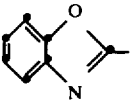 | —CH=CH—COOC$_2$H$_5$ | 290–291 |
| (2505) | 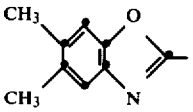 | —CH=CH—COOCH$_3$ | 230–231 |
| (2506) | 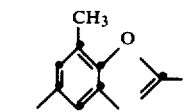 | —CH=CH—COOCH$_3$ | 184–185 |
| (2507) | 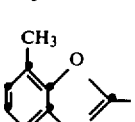 | —CH=CH—COOC$_2$H$_5$ | 183–184 |
| (2508) | 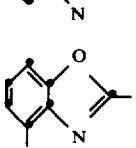 | —CH=CH—COOC$_2$H$_5$ | 197–198 |
| (2509) | 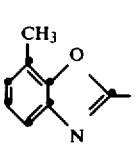 | —CH=CH—COOCH$_3$ | 200–244 |
| (2510) | 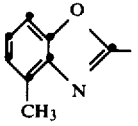 | —CH=CH—COOCH$_3$ | 217–238 |
| (2511) | 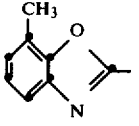 | —CH=CH—CN | 217–218 |
| (2512) | 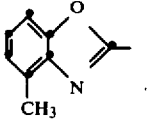 | —CH=CH—CN | 236–237 |
| (2513) | 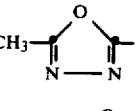 | —CH=CH—COOC$_2$H$_5$ | 192–194 |
| (2514) | 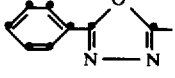 | —CH=CH—COOC$_2$H$_5$ | 223–226 |
| (2515) | 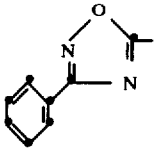 | —CH=CH—COOC$_2$H$_5$ | 231–233 |

TABLE VII-continued

| Compound | A | B | melting point °C. |
|---|---|---|---|
| (2516) | [benzotriazole fused with benzene] | —CH=CH—COOC$_2$H$_5$ | 242–243 |
| (2517) | 5,6-dimethoxy-benzotriazol-2-yl (CH$_3$O, CH$_3$O substituents) | —CH=CH—COOC$_2$H$_5$ | 301–302 |
| (2518) | 4-phenyl-1,2,3-triazol-2-yl | —CH=CH—COOC$_2$H$_5$ | 166–169 |
| (2519) | 3-methyl-1,2,4-oxadiazol-5-yl (CH$_3$ substituent) | —CH=CH—COOC$_2$H$_5$ | 174–175 |
| (2520) | 2-phenyl-1,2,3-triazol-4-yl | —CH=CH—COOC$_2$H$_5$ | 166–167 |
| (2521) | benzoxazol-2-yl | —CH=CH—CN | 259–260 |
| (2522) | —CN | —CH=CH—COOC$_2$H$_5$ | 147–148 |
| (2523) | 5-tert-butyl-benzoxazol-2-yl ((CH$_3$)$_3$C) | —CH=CH—COOC$_2$H$_5$ | 243–244 |
| (2524) | 4,6-dimethyl-benzoxazol-2-yl (CH$_3$, CH$_3$) | —CH=CH—CN | 232–233 |
| (2525) | 5-tert-butyl-benzoxazol-2-yl ((CH$_3$)$_3$C) | —CH=CH—CN | 240–241 |
| (2526) | benzoxazol-2-yl | —CH=C(CH$_3$)—COOC$_2$H$_5$ | 241–242 |
| (2527) | 6-methyl-benzoxazol-2-yl (CH$_3$) | —CH=C(CH$_3$)—COOC$_2$H$_5$ | 282–283 |
| (2528) | 4,6-dimethyl-benzoxazol-2-yl (CH$_3$, CH$_3$) | —CH=C(CH$_3$)—COOC$_2$H$_5$ | 147–148 |

TABLE VII-continued

| Compound | A | B | melting point °C. |
|---|---|---|---|
| (2529) | 5-tert-butyl-benzoxazol-2-yl | $-CH=C(CH_3)COOC_2H_5$ | 178-179 |
| (2530) | 7-methyl-benzoxazol-2-yl | $-CH=C(CH_3)COOC_2H_5$ | 121-122 |
| (2531) | 4-methyl-benzoxazol-2-yl | $-CH=C(CH_3)COOC_2H_5$ | 144-146 |
| (2532) | 3-phenyl-1,2,4-oxadiazol-5-yl | $-CH=CH-CN$ | 219-220 |
| (2533) | 3-methyl-1,2,4-oxadiazol-5-yl | $-CH=CH-CN$ | 166-167 |
| (2534) | 5-methyl-1,3,4-oxadiazol-2-yl | $-CH=CH-COOCH_3$ | 224-225 |
| (2535) | 5-phenyl-1,3,4-oxadiazol-2-yl | $-CH=CH-CN$ | 241-242 |
| (2536) | 5-methyl-1,3,4-oxadiazol-2-yl | $-CH=CH-CN$ | 214-215 |
| (2537) | phenyl | $-CH=C(CH_3)COOC_2H_5$ | 216-217 |
| (2538) | benzoxazol-2-yl | $-CH=C(CH_3)CN$ | 223-224 |
| (2539) | 3-isopropyl-1,2,4-oxadiazol-5-yl | $-CH=CH-CN$ | 177-178 |
| (2540) | 5-methyl-benzoxazol-2-yl | $-CH=C(CH_3)CN$ | 248-249 |
| (2541) | 5,7-dimethyl-benzoxazol-2-yl | $-CH=C(CH_3)CN$ | 183-184 |

TABLE VII-continued

| Compound | A | B | melting point °C. |
|---|---|---|---|
| (2542) | CH₃OCH₂-[N—O/N oxadiazole] | —CH=CH—CN | 163–165 |
| (2543) | [pyrido-oxazole with O, N] | —CH=CH—COOCH₃ | 274–275 |
| (2544) | CH₃OCH₂-[N=N/O oxadiazole] | —CH=CH—CN | 165–166 |
| (2545) | CH₃OCH₂-[N—N/O oxadiazole] | —CH=CH—COOCH₂CH₃ | 180–181 |
| (2546) | CH₃OCH₂-[N—O/N oxadiazole] | —CH=CH—COOCH₃ | 162–163 |
| (2547) | CH₃OCH₂-[N—O/N oxadiazole] | —CH=CH—COOCH₃CH₃ | 181–182 |
| (2548) | CH₃O-phenyl-[isoxazole N-O] | —CH=CH—COOCH₃ | 340–347 |
| (2549) | [pyrido-oxazole N,O,N] | —CH=CH—COOCH₃ | 288–289 |
| (2550) | [benzisoxazole O-N] | —CH=CH—COOCH₃ | 222–223 |
| (2551) | [phenyl-oxadiazole N=N/O] | —CH=C(CH₃)—CN | 226–227 |
| (2552) | [phenyl-oxazole N—O] | —CH=C(CH₃)—CN | 218–219 |
| (2553) | [pyrido-oxazole N,N,O] | —CH=CH—COOCH₃ | 277–278 |

The methyl 4-diethoxyphosphorylmethylphenylcinnamate used for the preparation of compound (2553) can be obtained in a manner similar to that described in German Offenlugungsschrift 2 602 750 for the preparation of the ethyl 4-diethoxyphosphorylmethylphenylcinnamate.

EXAMPLE 26

With stirring, 11.9 g of compound (2504) are dissolved at 110° C. in 500 ml of methyl cellosolve ®. A solution of 1.8 g of potassium hydroxide in 10 ml of water is added and the reaction mixture is stirred for 30 minutes at 110°–115° C. Then 3.5 ml of concentrated hydrochloric acid are added, the reaction mixture is cooled to 5° C., and the precipitated product is filtered washed with methanol and dried in vacuo at 60° C., affording 3 g of the compound of the formula

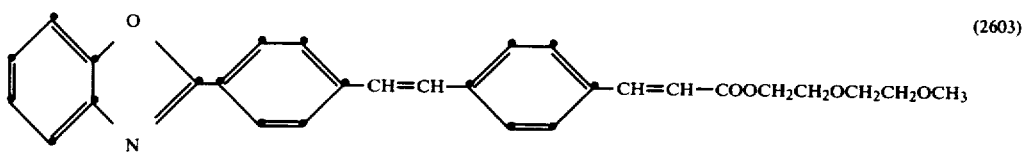

(2603)

with suction. The moist filter cake is stirred in 100 ml of water, and the product is isolated once more, washed with water and dried in vacuo at 60° C., affording 10.2 g of the compound of the formula which, after recrystallisation from 100 ml of xylene and 100 ml of nonane and afterwards from 500 ml of nonane with fuller's earth, is obtained in the form of a yellow crystalline powder with a melting pont of 258°-262° C.

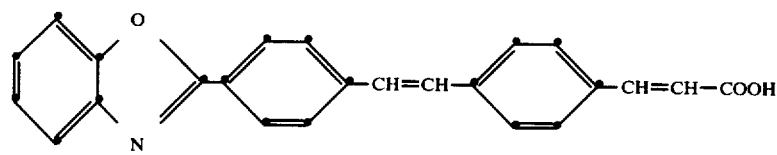

(2601)

in the form of a yellow crystalline powder with a melting point of 330°-332° C.

3.7 g of the above compound of the formula (2601) are stirred in 100 ml of toluene with 0.8 ml of thionyl chloride for 1 hour at 80°-85° C., with a further 3 additions of 0.8 ml of thionyl chloride at 15 minute intervals being made during this time. The reaction mixture is subsequently stirred for 5 hours at 105°-110° C. and cooled to 5° C. The crystallised product is filtered with suction, washed with hexane and dried in vacuo, afford-

EXAMPLE 27

About 23 g of sodium are dissolved in 200 ml of tetrahydrofuryl alcohol. With stirring, 3.9 g of compound (2504) are then added and the mixture is heated to 120°-125° C. and stirred for 1 hour at this temperature. The slightly turbid solution is filtered clear hot and the filtrate is cooled to room temperature. The crystallised product is filtered with suction and dried in vacuo at 60° C., affording 4.5 g of the compound of the formula

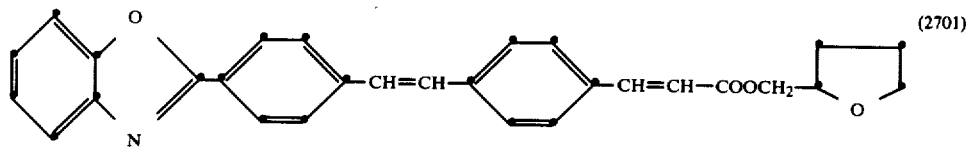

(2701)

ing 3.6 g of the compound of the formula which is recrystallised from 200 ml of boiling chloro-

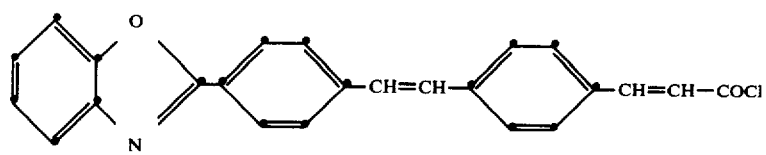

(2602)

in the form of a yellow powder with a melting point of 292°-293° C. (with decomposition).

3.6 g of the compound of the formula (2602) are stirred in 100 ml of diethylene glycol monomethyl ether for 1½ hours at 140° C. After cooling to room temperature, the crystallised product is filtered with suction, benzene, treatment with fuller's earth and addition of 200 ml of hexane, or from 220 ml of nonane. The pale yellow crystalline powder obtained has a melting point of 260°-262° C. The following compounds of the formula

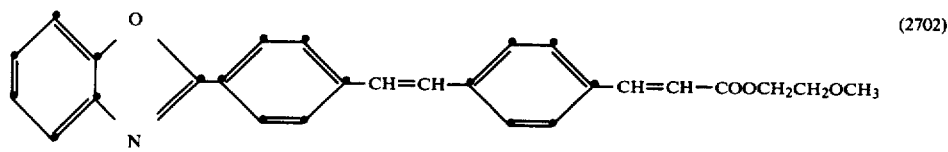

(2702)

can be obtained in similar manner. Melting point: 182° C.→solid→284° C. (conversion to another crystal modification);

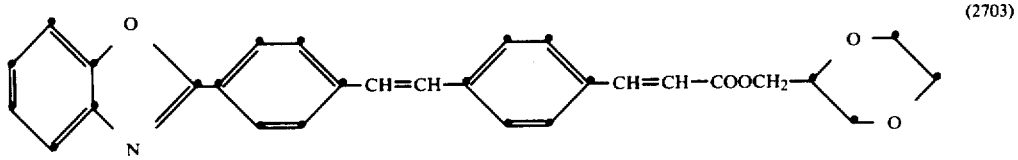
(2703)

Melting point: 276°–278° C.

EXAMPLE 28

With stirring, 6.5 g of the compound of the formula

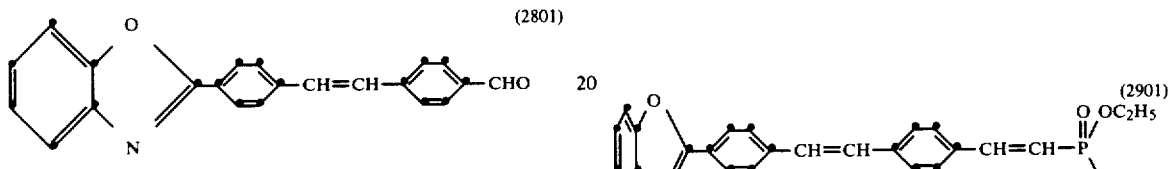
(2801)

are dissolved in 400 ml of dimethyl formamide at 50° C. Then 4.6 g of the phosphonate of the formula

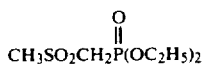

are added, followed by the dropwise addition of 4 g of a 30% solution of sodium methylate in methanol in the course of 10 minutes. Stirring is continued for 2 hours, then 400 ml of methanol are added and the mixture is cooled to 5° C. The crystallised product is filtered with suction and dried in vacuo. Four recrystallisations from chlorobenzene with the aid of fuller's earth yields 2.6 g of the compound of the formula

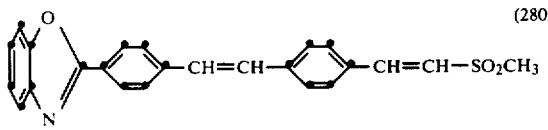
(2802)

in the form of a pale yellow powder with a melting point of 288°–289° C.

EXAMPLE 29

With stirring, 6.5 g of the compound of the formula (2801) are dissolved at 50° C. in 400 ml of dimethyl formamide. Then 5.8 g of the phosphonate of the formula

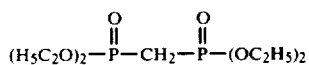

are added, followed by the dropwise addition of a solution of 0.5 g of sodium in 15 ml of anhydrous ethyl alcohol. Stirring is continued for 2 hours at 38°–40° C., then 400 ml of ethanol are added and the reaction mixture is cooled to 5° C. A small amount of insoluble product is removed by filtration. After dilution with 800 ml of water, the precipitated product is filtered with suction and dried in vacuo. Recrystallisation from 1000 ml of nonane with the aid of fuller's earth yields 3.5 g of the compound of the formula

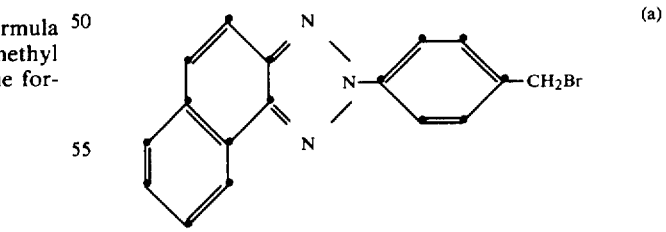
(2901)

in the form of a yellow crystalline powder with a melting point of 252°–253° C.

Preparation of the Starting Materials

The phosphonates used as starting materials are known or they can be obtained by methods known per se as described above or hereinafter, or, for example, as described in German Offenlegungsschrift 2 816 511 or 2 848 149.

A. 64.8 g of 2-(p-tolyl)naphth[1',2':4,5]-1,2,3-triazole are dissolved, with stirring, at 70°–75° C. in 1000 ml of carbon tetrachloride. While irradiating with UV light, 49 g of N-bromosuccinimide and 1,3 g of dibenzoyl peroxide are added in portions in the course of 21 minutes, and stirring is continued for 5 hours at 70°–75° C. After cooling to 4° C., the crystallised product is filtered with suction, washed with 250 ml of carbon tetrachloride, well pressed, and suspended in 500 ml of hot water. The suspension is filtered and the filter cake is washed with 7 liters of hot water and dried in vacuo at 90°–100° C., affording 42.8 g of the compound of the formula (a)

with a melting point of 225°–227° C.

189 g of the above compound are added, with stirring, at 140°–145° C. to 400 ml of triethylphosphite in the course of 1 hour, and stirring is continued for 6 hours at 145°–150° C. Excess triethylphosphite and ethyl diethylphosphonate formed during the reaction are distilled off from the reaction mixture in a water jet vacuum, affording as residue 209.5 g of the compound of the formula

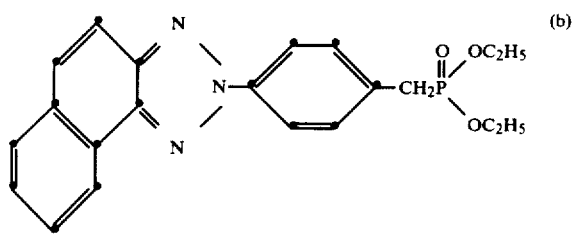

(b)

in the form of a viscous oil which crystallised completely after about 3 months.

B. With stirring, 11 g of acetamidoxime hydrochloride are suspended at room temperature in 200 ml of N-methylpyrrolidone. Then 8.4 g of sodium bicarbonate are added and the mixture is heated to 50° C. and subsequently stirred for 30 minutes without further heating. Then a further 8.4 g of sodium bicarbonate are added, followed by the addition of 18.9 g of 4-chloromethylbenzoyl chloride, whereupon the temperature again rises to 49° C. The reaction mixture is then heated to 160°–165° C. in the course of 10 minutes, kept for 5 minutes at this temperature, cooled, and poured into 1000 ml of water. The precipitate is collected by filtration, washed with water and dried in vacuo, affording 13.3 g of the compound of the formula

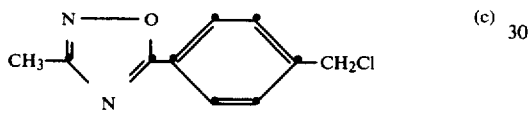

(c)

with a melting point of 89°–91° C.

23.9 g of this compound are heated in 37.5 g of triethylphosphite under nitrogen for 10 minutes to 210°–220° C. (bath temperature). Excess tributylphosphite is distilled off in vacuo, affording 38.4 g of the compound of the formula

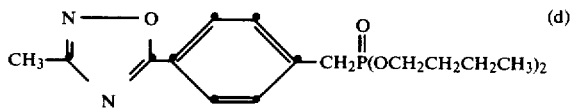

(d)

in the form of a reddish brown oil.

C. 66.7 g of acethydrazide are stirred at room temperature into 5000 ml of dioxane. After addition of 54 g of magnesium oxide, 170.1 g of 4-chloromethylbenzoyl chloride are slowly added. The reaction mixture is stirred for 18 hours at 40°–45° C. and filtered with suction. The residue is extracted with four 4 liter portions of dioxane and the product is recrystallised from 1000 ml of chlorobenzene, affording 123 g of the compound of the formula

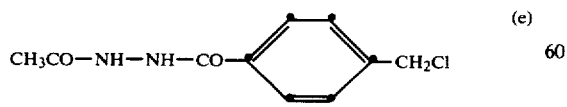

(e)

with a melting point of 174°–175° C.

With stirring, 45.2 g of this compound and 30.7 g of phosphoroxy chloride in 450 ml of cyclohexane are refluxed for 2 hours. Then a further 18.3 ml of phosphoroxy chloride and 250 ml of toluene are added and the mixture is refluxed for a further 3 hours. After addition of a further 250 ml of toluene, a small amount of tacky residue is decanted off and evaporated to dryness in vacuo, affording 32.5 g of the compound of the formula

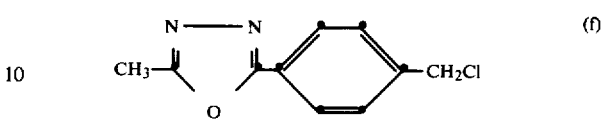

(f)

with a melting point of 73°–75° C.

32.5 g of this compound are heated in 78 g of tributylphosphite to 200° C. for 30 minutes under nitrogen. Excess tributylphosphite is then distilled off in vacuo, affording 57 g of the compound of the formula

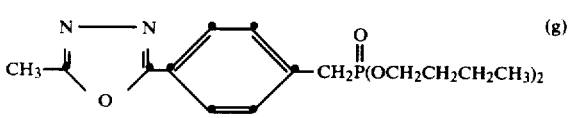

(g)

in the form of a brown oil which congeals after some time. The compounds of the formula

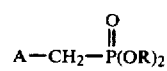

listed in the following table can be obtained in a manner similar to that described above:

| Compound | A | R | melting point °C. |
|---|---|---|---|
| h | CH₃O— (pyridazine-phenyl with two CH₃O groups) | —C₂H₅ | 154–156 |
| i | (phenyl-oxadiazole-phenyl) | —C₂H₅ | 119–121 |
| j | (phenyl-oxadiazole-phenyl, N—O) | —C₂H₅ | C. 60 (unsharp) |
| k | (phenyl-triazole-phenyl) | —C₂H₅ | oil |
| l | (CH₃)₂CH—oxadiazole | —C₄H₉(n) | oil |
| m | CH₃OCH₂—oxadiazole | —C₂H₅ | liquid |

-continued

| Compound | A | R | melting point °C. |
|---|---|---|---|
| n | (pyrimidine-phenyl structure with O) | —C$_2$H$_5$ | 124–125 |
| o | (isoxazole-phenyl with CH$_3$OCH$_2$) | —C$_4$H$_9$(n) | liquid |
| p | (CH$_3$O-phenyl-isoxazoline-phenyl) | —C$_2$H$_5$ | 120–121 |
| q | (pyrimidine-phenyl structure with O) | —CH$_3$ | oily; partly solid |
| r | (furan-phenyl structure) | —C$_2$H$_5$ | oily |

EXAMPLE 30

11 g of a 30% solution of sodium methylate in methanol are added dropwise at room temperature in the course of 15 minutes to a solution of 16 g of 2-(4-diethoxyphosphorylmethylphenyl)-5-methylpyrimidine and 9.5 g of methyl 4-formylcinnamate in 100 ml of dimethyl formamide, whereupon the temperature rises to 40° C. The reaction mixture is then stirred for 2 hours at 40° C., poured into a mixture of 160 ml of methanol and 250 ml of water, and the aqueous suspension is adjusted to pH 7 with acetic acid. The precipitate is filtered with suction and washed and dried. Repeated recrystallisation from o-dichlorobenzene with the aid of fuller's earth yields 9.5 g (53% of theory) of the compound of the formula

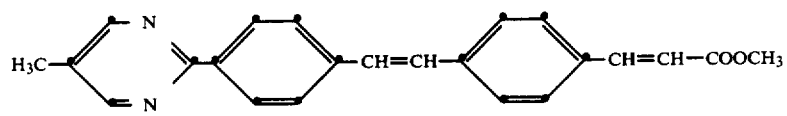

(3001)

in the form of a yellowish powder with a melting point of 270°–272° C.

The phosphonate of the formula

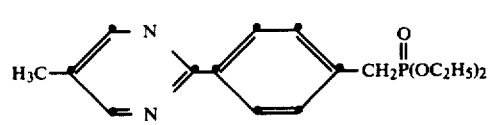

(3002)

employed for the synthesis is obtained as follows:

200 g of a 30% solution of sodium methylate in methanol are added dropwise at 50° C. in the course of 45 minutes to a solution of 170 g of p-tolylamidine hydrochloride and 125 g of 3-ethoxy-2-methyl-acrolein in 500 ml of methanol. The reaction mixture is then stirred for 4 hours at 50° C. and poured into 2000 ml of water. The precipitate is filtered with suction, washed with water and dried, affording 153 g (83% of theory) of 2-(4-methylphenyl)-5-methylpyrimidine with a melting point of 122°–123° C.

Reaction of the above 2-(4-methylphenyl)-5-methylpyrimidine with N-bromosuccinimide, as described in Example 15, affords 2-(4-bromomethylphenyl)-5-methylpyrimidine with a melting point of 129°–131° C. (recrystallisation from ligroin). With stirring, a mixture of 184 g of 2-(4-bromomethylphenyl)-5-methylpyrimidine and 465 g of triethylphosphite is slowly heated to 150° C., while simultaneously distilling off ethyl bromide, and then stirred for 5 hours at this temperature. Excess triethylphosphite is distilled off, affording 220 g of the phosphonate in the form of a light brown viscous oil.

EXAMPLE 31

Polyester fabric (Terylene ® 540) is treated in a dyeing machine, at a liquor ratio of 1:20, with an aqueous bath which contains 0.1% based on the weight of the goods of the compound of the formula (101), (108), (401), (1501) or (1701), and 1 g/liter of the condensation product of 35 moles of ethylene oxide and 1 mole of stearyl alcohol. The bath is then heated from 40° to 120° C. in the course of 30 minutes, kept at this temperature for 30 minutes, and then cooled to 15° C. in the course of 15 minutes. The fabric is then rinsed in running deionised water and dried at 70° C. An excellent white effect is obtained on the treated fabric.

EXAMPLE 32

Polyester fabric (Terylene ® 540) is padded at room temperature with a liquor which contains 1 g/1 of the compound of the formula (901), (2302), (2502), (2508), or (1601), and 1 ml of the condensation product of 8–9 moles of ethylene oxide and 1 mole of p-tert-octylphenol. The liquor pick-up is 80%. The fabric is then dried for 10 minutes at 80° C. and subsequently thermofixed at 200° C. for 30 seconds. A good white effect is obtained on the treated fabric.

EXAMPLE 33

A polyester/cotton blend is treated in a dyeing machine, at a liquor ratio of 1:20, with an aqueous bath which contains 0.1%, based on the weight of the goods, of the compound of the formula (104), (901), (907), (904) or (1507), and 1 g/liter of the condensation product of 35 moles of ethylene oxide and 1 mole of stearyl alcohol. The bath is then heated from 40° to 97° C. in the course of 30 minutes, kept at this temperature for 30 minutes, and then cooled to 15° C. in the course of 15 minutes. The fabric is then rinsed in running deionised water and dried at 70° C. A good white effect is obtained on the treated polyester/cotton blend.

EXAMPLE 34

Polyamide 6.6 woven jersey fabric is treated in a dyeing machine, at a liquor ratio of 1:20, with an aqueous bath which contains 0.2%, based on the weight of the goods, of the compound (601), (901), (1601), or (2507) and 3 g/liter of a mixture of 60 parts by weight of sodium hydrosulfite and 40 parts by weight of sodium pyrophosphate. The bath is heated from 40° to 130° C. in the course of 30 minutes, kept at this temperature for 30 minutes and then cooled to 15° C. in the course of 15 minutes. The fabric is then rinsed in running deionised water and dried at 60° C. A good white effect is obtained on the treated polyamide fabric.

EXAMPLE 35

Triacetate fabric is treated in a dyeing machine, at a liquor ratio of 1:20, with an aqueous bath which contains 0.1% based on the weight of the goods, of the compound of the formula (301), (501), (601), or (901), and 1 g/liter of the condensation product of 35 moles of ethylene oxide and 1 mole of stearyl alcohol. The bath is then heated from 40° to 97° C. in the course of 30 minutes, kept at this temperature for 30 minutes, and then cooled to 30° C. in the course of 15 minutes. The fabric is then rinsed in running deionised water and dried at 60° C. A good white effect is obtained on the treated triacetate fabric.

EXAMPLE 36

Acetate satin fabric is treated in a dyeing machine, at a liquor ratio of 1:20, with an aqueous bath which contains 0.1%, based on the weight of the goods, of the compound of the formula (903), (1001), (1507), (1602) or (2513), 1 g/liter of the condensation product of 35 moles of ethylene oxide and 1 mole of stearyl alcohol, and 0.5 ml/liter of 80% acetic acid. The bath is then heated from 40° to 80° C. in the course of 30 minutes, kept at this temperature for 30 minutes, and then cooled to 20° C. in the course of 15 minutes. The fabric is then rinsed in running deionised water and dried at 60° C. A good white effect is obtained on the treated acetate satin fabric.

EXAMPLE 37

1000 g of polyester granules of the ethylene glycol terephthalate type, containing 0.5% of TiO$_2$(anatase type), are mixed with 0.5 g of a compound of the formula (101), (106), (901) or (904) in a rotary wheel mixer, and the treated granules are spun in an extruder at 280° C. to a multifilament. The excellent white effect obtained on the filaments has good lightfastness.

EXAMPLE 38

100 parts of polystyrene, containing about 1.5% of TiO$_2$ (rutile type), and 0.05 part of a compound of the formula (1506), (1505), (1601), or (2515) are mixed dry and the mixture is processed in an extruder at 180° C. to give whitened granules. The granules are moulded to small sheets in an injection moulding machine. The strong white effect obtained on the sheets has good lightfastness.

EXAMPLE 39

A homogeneous mixture of 65 parts of polyvinyl chloride (suspension type), 32 parts of dioctyl phthalate, 3 parts of an epoxidised soya bean oil, 1.5 parts of a stabiliser, 0.5 part of a co-stabiliser, 5 parts of TiO$_2$ (rutile type) and 0.05 part of a compound of the formula (105), (106), (701), (902) or (1504) is rolled on a calender at 150° C. to a film. The strong white effect obtained has good lightfastness.

EXAMPLE 40

Polyester fabric (Terylene ® 540) is treated in a dyeing machine, at a liquor ratio of 1:20, with an aqueous bath which contains 0.1%, based on the weight of the fabric, of a mixture of the fluorescent whitening agent of the formula (2502) and that of the formula

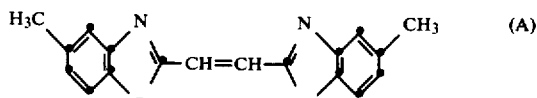

in the ratio 1:2, and 1 g/l of the adduct of 35 moles of ethylene oxide and 1 mole of stearyl alcohol. The application is effected in accordance with the following programme: from 40° to 120° C. in 30 minutes, at 120° C. over 30 minutes, and from 40° to 120° C. in 15 minutes. The fabric is then rinsed with running deionised water and dried with an iron of 180°–190° C. The white effect obtained on the treated fabric is stronger than that obtained with the individual mixture components. A stronger white effect is also obtained with a mixture containing the compound of the formula (2502) and the compound (A) in the ratio 2:1.

EXAMPLE 41

Polyester fabric (Terylene ® 540) is treated at room temperature with an aqueous liquor which contains 1 g/l of a mixture consisting of the fluorescent whitening agent of the formula (1601) and that of the formula

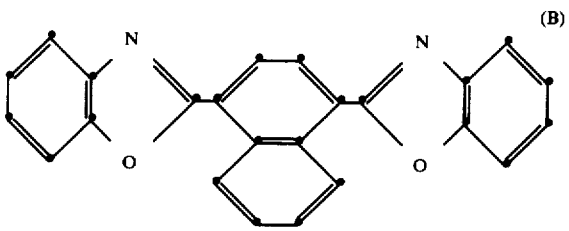

in the ratio 1:2 and 2:1 respectively, and 1 g/l of the adduct of 8 to 9 moles of ethylene oxide and 1 mole of p-tert-octylphenol. The liquor pick-up is 80° C. The fabric is subsequently dried for 10 minutes at 80° C. and thermofixed for 30 seconds at 180° C. The white effect obtained on the treated fabric is stronger than that obtained with the individual mixture components.

What is claimed is:

1. A 4-heterocyclyl-4'-stilbene of the formula

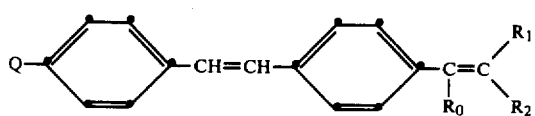

wherein Q is a monocyclic 5- or 6-membered aromatic heterocyclic ring containing nitrogen or containing nitrogen and oxygen, which is unsubstituted or substituted by non-chromophoric groups and which contains 0, 1 or 2 fused benzene rings, or is a bicyclic 9-membered aromatic heterocylic ring, phenyl which is unsubstituted or substituted by non-chromophoric groups, or is cyano, carboxyl, alkoxycarbonyl, alkylsulfonyl or arylsulfonyl, $R_0$ is hydrogen, or alkyl which is unsubstituted or substituted by non-chromophoric groups, $R_1$ is hydrogen, or is alkyl, alkoxycarbonyl, carbamoyl or sulfonamide, each of which is unsubstituted or substituted by non-chromophoric groups, or is alkenyl, carboxyl, alkylsulfonyl, arylsulfonyl, aralkylsulfonyl, cyano, sulfo or phosphonic acid dialkyl ester, and $R_2$ is hydrogen, or is alkyl or alkenyl, each of which is unsubstituted or substituted by non-chromophoric groups, with the proviso that at most one of $R_1$ and $R_2$ is hydrogen.

2. A 4-heterocyclyl-4′-vinylstilbene according to claim 1 of the formula

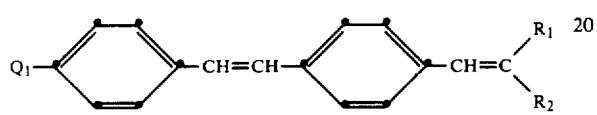

wherein $Q_1$ is phenyl which is unsubstituted or substituted by non-chromophoric groups, or is cyano, alkoxycarbonyl, alkylsulfonyl or arylsulfonyl, or a radical of the formula

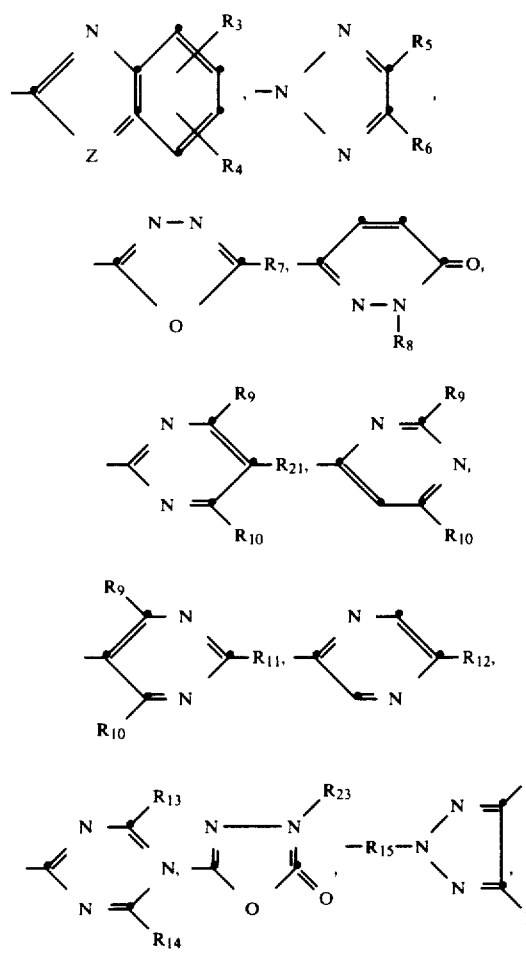

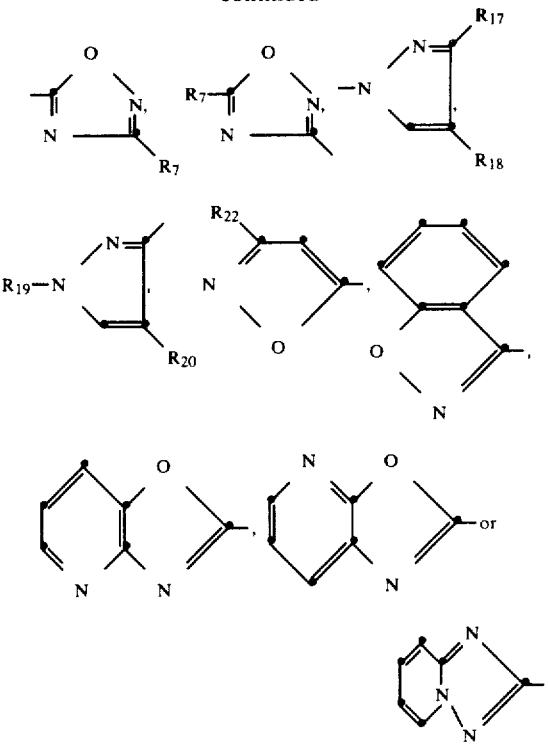

in which formulae $R_3$ is hydrogen, chlorine, $C_1-C_4$alkyl, phenyl($C_1-C_3$)alkyl, cyclohexyl, phenyl, $C_1-C_4$alkoxy, $C_1-C_4$alkylsulfonyl, $C_1-C_4$ alkoxycarbonyl, cyano or carboxyl, or together with $R_4$ is a fused 1-cyclopentene, 1-cyclohexene or benzene ring, each of which is unsubstituted or substituted by 1 to 4 methyl groups, $R_4$ is hydrogen, chlorine or $C_1-C_4$alkyl or, together with $R_3$, forms a 1-cyclopentene, 1-cyclohexene or benzene ring, each of which is unsubstituted or substituted by 1 to 4 methyl groups, $R_5$ is hydrogen, $C_1-C_4$alkyl, cyano, COOR, wherein R is $C_1-C_4$alkyl, phenyl or styryl or, together with $R_6$, forms a fused benzene ring which is unsubstituted or substituted by $C_1-C_4$alkyl, $C_1-C_4$alkoxy or chlorine, or a fused naphthalene ring, $R_6$ is hydrogen, $C_1-C_4$alkyl, phenyl or, together with $R_5$ forms a fused benzene ring which is unsubstituted or substituted by $C_1-C_4$alkyl, $C_1-C_4$alkoxy or chlorine, or a fused naphthalene ring, $R_7$ is $C_1-C_4$alkyl which is unsubstituted or substituted by non-chromophoric groups, phenyl, styryl, biphenylyl or naphthyl, each of which is unsubstituted or substituted by $C_1-C_4$alkyl, $C_1-C_4$alkoxy, $C_1-C_4$alkoxycarbonyl, cyano or chlorine, $R_8$ is hydrogen, $C_1-C_4$alkyl or phenyl which is unsubstituted or substituted by chlorine or methyl, $R_9$ and $R_{10}$, each independently of the other, is hydrogen, $C_1-C_4$alkyl, phenyl which is unsubstituted or substituted by chlorine or methyl, or is $C_1-C_4$alkoxy, $C_3-C_8$alkoxyalkoxy, phenoxy which is unsubstituted or substituted by chlorine or methyl, or is chlorine, $C_1-C_4$alkylthio, phenylthio, $C_1-C_4$alkylamino, di($C_1-C_4$)alkylamino, morpholino, piperidino, piperazino, pyrrolidino or anilino, R₁₁ is hydrogen, C₁-C₄alkyl or phenyl which is unsubstituted or substituted by chlorine or methyl, R₁₂ is C₁-C₄alkoxy, C₃-C₈alkoxyalkoxy, C₁-C₄alkylthio, phenoxy which is unsubstituted or substituted by chlorine or methyl, or is cycloalkoxy, C₁-C₄alkylthio, phenylthio which is unsubstituted or substituted by chlorine or methyl, or is C₁-C₄alkylamino, di(C₁-C₄)alkylamino, morpholino, piperidino, piperazino, pyrrolidino or anilino, R₁₃ and R₁₄ are hydrogen, halogen, C₁-C₄alkoxy, phenyl, aralkoxy, cycloalkoxy, aryloxy, C₁-C₄alkylmercapto, C₁-C₄-alkylamino, di(C₁-C₄)alkylamino, morpholino, piperidino, piperazino, pyrrolidino, arylamino or C₁-C₄alkyl, R₁₅ is phenyl which is unsubstituted or substituted by chlorine or C₁-C₄alkyl, R₁₆ is hydrogen or C₁-C₄alkyl, R₁₇ is phenyl which is unsubstituted or substituted by chlorine or C₁-C₄alkyl, R₁₈ is hydrogen or C₁-C₄alkyl, R₁₉ is phenyl which is unsubstituted or substituted by chlorine or C₁-C₄alkyl, R₂₀ is hydrogen or C₁-C₄alkyl, R₂₁ is hydrogen or C₁-C₄alkyl, R₂₂ is phenyl which is unsubstituted or substituted by C₁-C₄alkoxy, R₂₃ is hydrogen, C₁-C₄alkyl or phenyl which is unsubstituted or substituted by C₁-C₄alkyl, halogen or cyano, and Z is O, S or NX, wherein X is hydrogen, C₁-C₄alkyl, acetyl, benzoyl or phenyl.

3. A 4-heterocyclyl-4'-vinyl stilbene according to claim 2 of the formula

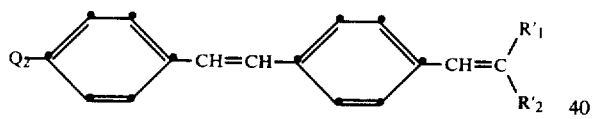

wherein $R_1'$ is hydrogen, $C_1$-$C_6$alkyl, $C_1$-$C_6$alkyl which is substituted by $C_1$-$C_4$alkoxy or $C_2$-$C_5$alkoxycarbonyl, or is $C_2$-$C_4$alkenyl, cyano, COOR$^o$, wherein R$^o$ is $C_1$-$C_4$alkyl, $C_1$-$C_4$alkoxy-$C_2$-$C_4$alkyl, $C_1$-$C_4$alkoxy-$C_2$-$C_4$alkoxy-$C_2$-$C_4$alkyl, $C_1$-$C_4$alkoxy-$C_2$-$C_4$alkoxy-$C_2$-$C_4$alkoxy-$C_2$-$C_4$alkyl, tetrahydro-2-furylmethyl, 1,4-dioxa-2-cyclohexylmethyl, allyl, $C_1$-$C_4$alkylamino-$C_1$-$C_4$alkyl or di($C_1$-$C_4$)alkylamino-$C_1$-$C_4$alkyl, -CON(R')(R''), wherein R' is hydrogen, $C_1$-$C_6$alkyl, $C_2$-$C_6$alkyl which is substituted by hydroxyl, $C_1$-$C_4$alkoxy, $C_2$-$C_6$hydroxyalkoxy, -SO₃M or di($C_1$-$C_4$)alkylamino, or is cyclohexyl, benzyl or phenethyl, and R'' is hydrogen, $C_1$-$C_6$alkyl, $C_2$-$C_6$alkyl which is substituted by hydroxyl, $C_1$-$C_4$alkoxy or $C_2$-$C_6$hydroxyalkoxy, -SO₂N(R')(R''), wherein R' and R'' are as defined above, -SO₃M, $R_x$-SO₂-, wherein $R_x$ is $C_1$-$C_6$alkyl, $C_2$-$C_6$alkyl which is substituted by hydroxyl, $C_1$-$C_4$alkoxy or $C_1$-$C_4$alkoxy-$C_2$-$C_6$alkoxy, or is phenyl or benzyl or phosphonic acid dialkyl ester;

$R_2'$ is hydrogen or $C_1$-$C_6$alkyl,

M is hydrogen or a non-chromophoric cation

Q₂ is phenyl, phenyl which is substituted by halogen, C₁-C₄alkyl, C₁-C₄alkoxy, carboxyl, C₂-C₅alkoxycarbonyl or cyano, or is cyano, carboxyl, C₂-C₅alkoxycarbonyl or $R_x$-SO₂-, wherein $R_x$ is as defined above, or is a radical of the formula

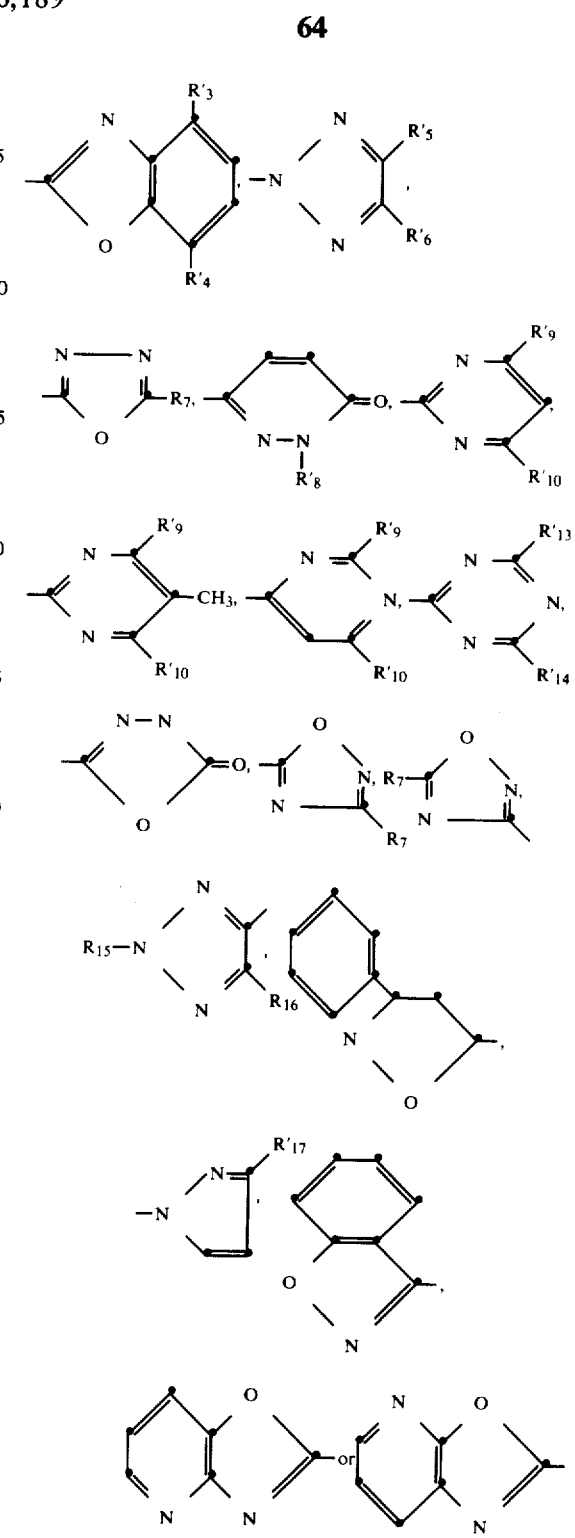

in which formulae

R₃' is hydrogen, methyl, chlorine or C₁-C₄alkoxy,

R₄' is hydrogen, chlorine, C₁-C₄alkyl, phenyl, C₁-C₄alkoxy or phenoxy,

R₅' is hydrogen, C₁-C₄alkyl, phenyl or styryl or, together with R₆, forms a fused unsubstituted benzene ring or a fused benzene ring which is substituted by C₁-C₄alkyl, C₁-C₄alkoxy or chlorine, or a fused naphthalene ring, $R_6'$ is hydrogen, $C_1-C_4$alkyl, phenyl or, together with $R_5'$, forms a fused unsubstituted benzene ring or a fused benzene ring which is substituted by $C_1-C_4$alkoxy, $C_1-C_4$alkoxy or chlorine, or a fused naphthalene ring, $R_7$ is $C_1-C_4$alkyl which is unsubstituted or substituted by non-chromophoric substituents, phenyl, styryl, biphenyl or naphthyl, each of which is unsubstituted or substituted by $C_1-C_4$alkyl, $C_1-C_4$alkoxy, $C_1-C_4$alkoxycarbonyl, cyano or chlorine, $R_8'$ is unsubstituted $C_1-C_4$alkyl or phenyl, $R_9'$ is hydrogen, unsubstituted $C_1-C_4$alkyl, phenyl which is unsubstituted or substituted by chlorine or methyl, or is chlorine, $C_1-C_4$alkoxy, $C_3-C_5$alkoxyalkoxy, phenoxy which is unsubstituted or substituted by chlorine or methyl, or is $C_1-C_4$alkylthio or phenylthio, $R_{10}'$ is hydrogen, unsubstituted $C_1-C_4$alkyl, $C_1-C_4$alkoxy, phenyl which is unsubstituted or substituted by chlorine or methyl, phenoxy which is unsubstituted or substituted by chlorine or methyl, or is $C_1-C_4$alkylthio, phenylthio or chlorine, $R_{13}'$ and $R_{14}'$ are hydrogen, $C_1-C_4$alkylamino, di($C_1-C_4$)alkylamino, phenyl, morpholino, piperidino, phenylamino or a radical $-(OCH_2-CH_2)_q-OY$, wherein Y is hydrogen, $C_1-C_4$alkyl, benzyl or phenyl, and q is an integer from 0 to 7, $R_{15}$ is phenyl which is unsubstituted or substituted by chlorine or $C_1-C_4$alkyl, $R_{16}$ is hydrogen or $C_1-C_4$alkyl, and $R_{17}'$ is $C_1-C_4$alkyl.

4. A 4-heterocyclyl-4'-vinylstilbene according to claim 3 of the formula

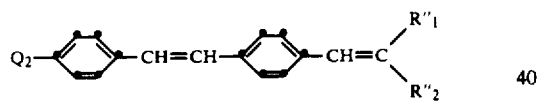

wherein $R_1''$ is cyano, COOR, wherein R is $C_1{-}^{14}$ $C_4$alkyl, $C_1-C_4$alkoxy-$C_2-C_4$alkyl, $C_1-C_4$alkoxy-$C_2-C_4$alkoxy-$C_2-C_4$alkyl, $C_1-C_4$alkoxy-$C_2-C_4$alkoxy-$C_2{}^{14}$ $C_4$alkoxy-$C_2-C_4$alkyl, 2,3,4,5-tetrahydro-2-furylmethyl, 1,4-dioxa-2-cyclohexylmethyl, CON(R')(R''), wherein R' is hydrogen, $C_1-C_6$alkyl, $C_2-C_6$alkyl which is substituted by hydroxyl, $C_1-C_4$alkoxy, $C_2-C_6$hydroxyalkoxy, $-SO_3M$ or mono- or di($C_1-C_4$)alkylamino, or is cycloalkyl, benzyl or phenethyl, and R'' is hydrogen, $C_1-C_6$alkyl, $C_2-C_6$-alkyl which is substituted by hydroxyl, $C_1-C_4$alkoxy or $C_2-C_6$hydroxyalkoxy, $R_x-SO_2-$, wherein $R_x$ is $C_1-C_6$alkyl, $C_2-C_6$alkyl which is substituted by $C_1-C_4$alkoxy or $C_1-C_4$alkoxy-$C_2-C_6$alkoxy, or is phenyl or benzyl or phosphonic acid dialkyl ester; and $R_2''$ is hydrogen or $C_1-C_4$alkyl.

5. A 4-heterocyclyl-4'-vinylstilbene according to claim 4 of the formula

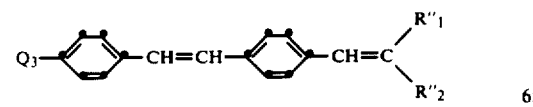

wherein $Q_3$ is phenyl, $C_2-C_5$alkoxycarbonyl, cyano or a radical of the formula

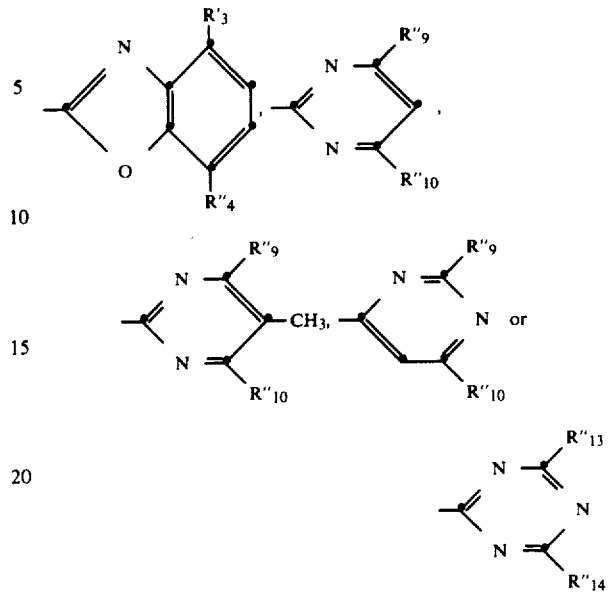

in which formulae $R_3'$ is hydrogen, methyl, chlorine or $C_1-C_4$alkoxy, $R_4''$ is hydrogen, methyl, chlorine or $C_1-C_4$alkyl, $R_9''$ is hydrogen, methyl, phenyl, $C_1-C_3$alkoxy, methoxyethoxy or phenoxy, $R_{10}''$ is unsubstituted alkyl of 1 or 2 carbon atoms, $C_1-C_3$alkoxy or phenoxy, and each of $R_{13}''$ and $R_{14}''$ is hydrogen or a radical $-(OCH_2-CH_2)_r-OY'$, wherein Y' is $C_1-C_4$alkyl and r is an integer from 0 to 2.

6. A 4-heterocyclyl-4'-vinylstilbene according to claim 5 of the formula

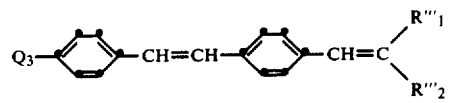

wherein $R_1'''$ is cyano, COOR, wherein R is $C_1-C_4$alkyl, $C_1-C_4$-alkoxy-$C_2-C_4$alkyl, $C_1-C_4$alkoxy-$C_2-C_4$alkoxy-$C_2-C_4$alkyl, $C_1-C_4$alkoxy-$C_2-C_4$alkoxy-$C_2-C_4$alkoxy-$C_2-C_4$alkyl, 2,3,4,5-tetrahydro-2-furylmethyl or 1,4-dioxa-2-cyclohexylmethyl or $R_x-SO_2-$, wherein $R_x$ is $C_1-C_4$alkyl, $C_2-C_6$alkyl which is substituted by $C_1-C_4$alkoxy or $C_1-C_4$alkoxy-$C_2-C_6$alkoxy, or is phenyl or benzyl, and $R_2'''$ is hydrogen or $C_1-C_4$alkyl.

7. A 4-heterocyclyl-4'-vinylstilbene according to claim 5 of the formula

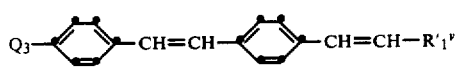

wherein $R_1'^v$ is cyano or COOR', and wherein R' is $C_1-C_4$alkyl or $C_1-C_4$alkoxy-$C_2-C_6$alkyl.

8. The 4-heterocyclyl-4'-vinylstilbene according to claim 6 of the formula

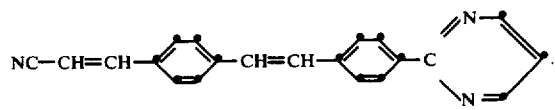

9. The 4-heterocyclyl-4'-vinylstilbene according to claim 6 of the formula

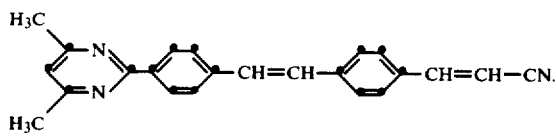

10. The 4-heterocyclyl-4'-vinylstilbene according to claim 6 of the formula

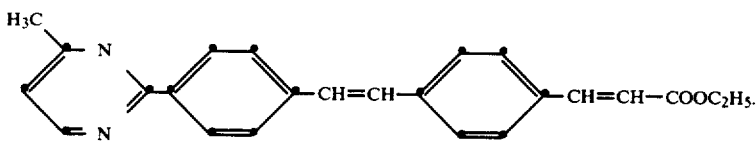

11. The 4-heterocyclyl-4'-vinylstilbene according to claim 6 of the formula

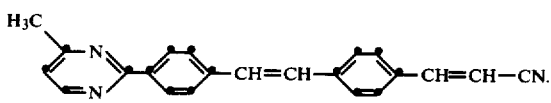

12. The 4-heterocyclyl-4'-vinylstilbene according to claim 6 of the formula

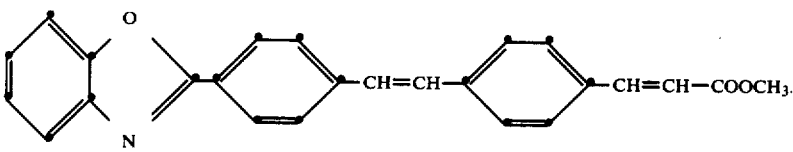

13. A process for the production of 4-heterocyclyl-4'-vinylstilbene of the formula

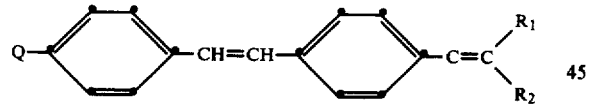

wherein Q is a monocyclic 5- or 6-membered aromatic heterocyclic ring, containing nitrogen or containing nitrogen and oxygen, which is unsubstituted or substituted by non-chromophoric groups and which contains 0, 1 or 2 fused benzene rings, or is a bicyclic 9-membered aromatic heterocyclic ring, phenyl which is unsubstituted or substituted by non-chromophoric groups, or is cyano, carboxyl, alkoxycarbonyl, alkylsulfonyl or aryl sulfonyl, $R_0$ is hydrogen, or alkyl which is unsubstituted or substituted by non-chromophoric groups, $R_1$ is hydrogen, or is alkyl, alkoxycarbonyl, carbamoyl or sulfonamide, each of which is unsubstituted or substituted by non-chromophoric groups, or is alkenyl, carboxyl, alkylsulfonyl, arylsulfonyl, aralkylsulfonyl, cyano, sulfo or phosphonic acid dialkyl ester, and $R_2$ is hydrogen, or is alkyl or alkenyl, each of which is unsubstituted or substituted by non-chromophoric groups, with the proviso that at most one of $R_1$ and $R_2$ is hydrogen, which process comprises condensing, in the presence of an organic solvent and of a basic condensation agent, a compound of the formula

with a compound of the formula

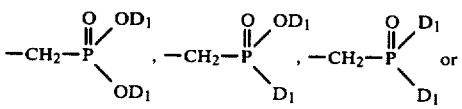

in which formulae, Q, $R_0$, $R_1$ and $R_2$ are as defined above and one of $Z_1$ and $Z_2$ is the OHC group and the other is a grouping of the formula $$-CH_2-\overset{\overset{O}{\|}}{P}\diagup^{OD_1}_{OD_1} \ , \ -CH_2-\overset{\overset{O}{\|}}{P}\diagup^{OD_1}_{D_1} \ , \ -CH_2-\overset{\overset{O}{\|}}{P}\diagup^{D_1}_{D_1} \ or$$

$$-CH=P\diagup^{D_1}_{\diagdown D_1}^{-D_1}$$

wherein $D_1$ is an unsubstituted or a substituted alkyl, aryl, cycloalkyl or aralkyl radical.

14. A process for whitening man-made, regenerated man-made and natural organic material of high molecular weight, which comprises incorporating in or applying to the surface of said material a 4-heterocyclyl-4'-vinylstilbene as defined in any one of claims 1 to 7, in an amount of 0.001 to 2%, based on the weight of said material.

15. A process according to claim 14, wherein the material to be whitened is organic material of high molecular weight.

16. A process according to claim 14, wherein the material to be whitened is polyester.

17. A mixture containing a 4-heterocyclyl-4'-vinylstilbene according to any one of claims 1 to 7, and a fluorescent whitening agent suitable for polyester, in the ratio of 1:9 to 9:1.

18. A mixture according to claim 17 containing a 4-heterocyclyl-4'-vinylstilbene of the formula

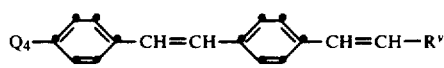

wherein Q₄ is a benzoxazol-2-yl radical, a pyrimidin-2-yl radical, a 4-methylpyrimidin-2-yl radical or a 4,6-dimethylpyrimidine-2-yl radical, and R$^v$ is $C_2$–$C_4$alkoxycarbonyl or cyano, and, as fluorescent whitening agent suitable for polyester, 1,4-bis(benzoxazol-2'-yl)-naphthalene, 4,4'-bis-(ethoxycarbonylvinyl)-stilbene, 4,4'-bis-(cyanovinyl)-stilbene, 1,4-bis(2'-cyanostyryl)-benzene, 1,5-bis(benzoxazole-2'-yl)-thiophene, 1-phenyl-4-(5',7'-dimethylbenzoxazol-2'-yl)-stilbene, 1,2-bis-(5'-methylbenzoxazol-2'-yl)-vinylene, 4-(benzoxazol-2'-yl)-4'-(3''-methyl-1'',2'',4''-oxadiazol-5''-yl)-stilbene and 2,4-dimethoxytriazine-6-ylpyrene in the ratio 1:2 or 2:1.

19. A mixture according to claim 18 containing the fluorescent whitening agent of the formula

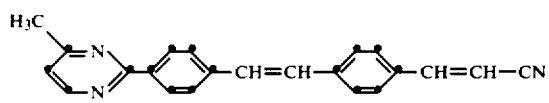

and the fluorescent whitening agent of the formula

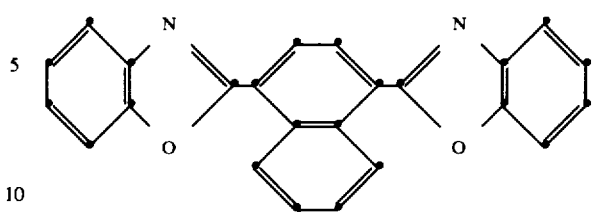

in the ratio 1:2 or 2:1.

20. A mixture according to claim 17 containing the fluorescent whitening agent of the formula

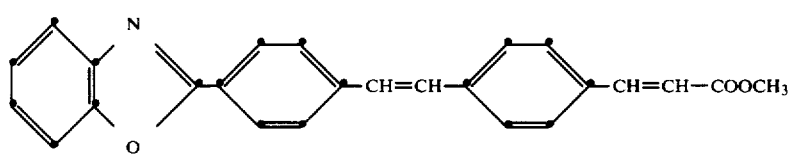

and the fluorescent whitening agent of the formula

in the ratio 1:2 or 2:1.

* * * * *